US010271895B2

(12) United States Patent
Batchelor et al.

(10) Patent No.: US 10,271,895 B2
(45) Date of Patent: *Apr. 30, 2019

(54) COMBINATION ELECTROSURGICAL DEVICE

(71) Applicant: GYRUS ACMI, INC., Southborough, MA (US)

(72) Inventors: Kester J. Batchelor, Mound, MN (US); Nikhil M. Murdeshwar, Maple Grove, MN (US); Jyue Boon (Jonas) Lim, New Brighton, MN (US); Dennis G. Lamser, Marlborough, MA (US); Tsuyoshi Hayashida, Maple Grove, MN (US); Richard J. Curtis, Maple Grove, MN (US); Theodore Blus, Shoreview, MN (US); Riyad Moe, Madison, WI (US); Ryan Windgassen, Nowthen, MN (US)

(73) Assignee: GYRUS ACMI INC, Southborough, MA (US)

( * ) Notice: Subject to any disclaimer, the term of this patent is extended or adjusted under 35 U.S.C. 154(b) by 275 days.

This patent is subject to a terminal disclaimer.

(21) Appl. No.: 15/235,506

(22) Filed: Aug. 12, 2016

(65) Prior Publication Data
US 2016/0346033 A1 Dec. 1, 2016

Related U.S. Application Data

(63) Continuation of application No. 14/210,535, filed on Mar. 14, 2014, now Pat. No. 9,452,009.
(Continued)

(51) Int. Cl.
A61B 18/12 (2006.01)
A61B 18/14 (2006.01)
A61B 18/00 (2006.01)

(52) U.S. Cl.
CPC ...... *A61B 18/1442* (2013.01); *A61B 18/1402* (2013.01); *A61B 2018/0091* (2013.01);
(Continued)

(58) Field of Classification Search
CPC ............ A61B 18/1402; A61B 18/1442; A61B 2018/00607; A61B 2018/0091;
(Continued)

(56) References Cited

U.S. PATENT DOCUMENTS 1,198,958 A 9/1916 Risely
2,042,985 A 6/1936 Gardella
(Continued)

FOREIGN PATENT DOCUMENTS

CN 1149519 A 5/1997
CN 102164556 A 8/2011
(Continued)

OTHER PUBLICATIONS

Japanese Office Action for Application No. 2016-502290 drafted Aug. 24, 2016.
(Continued)

*Primary Examiner* — Daniel W Fowler
(74) *Attorney, Agent, or Firm* — The Dobrusin Law Firm, P.C.; Daniel P. Aleksynas

(57) ABSTRACT

An electrosurgical device: forceps having: a first working arm, a second working arm, wherein the electrosurgical device has a first electrosurgical configuration where the first working arm and the second working arm are in an opposed position so that the forceps deliver a first therapy current that flows between the first working arm and the second working arm; and wherein the electrosurgical device has a second electrosurgical configuration when the first working arm, the second working arm, or both are repositionable relative to each other so that the first working arm is extended with
(Continued)

respect to the second working arm or vice versa and a second therapy current is delivered from the first working arm to a remote electrode.

18 Claims, 13 Drawing Sheets

Related U.S. Application Data

(60) Provisional application No. 61/864,157, filed on Aug. 9, 2013, provisional application No. 61/787,731, filed on Mar. 15, 2013.

(52) U.S. Cl.
CPC ............ *A61B 2018/00607* (2013.01); *A61B 2018/00922* (2013.01); *A61B 2018/00928* (2013.01); *A61B 2018/00946* (2013.01); *A61B 2018/00958* (2013.01); *A61B 2018/126* (2013.01); *A61B 2018/1253* (2013.01); *A61B 2018/1457* (2013.01); *A61B 2018/1462* (2013.01); *A61B 2018/1475* (2013.01)

(58) Field of Classification Search
CPC ........... A61B 2018/00922; A61B 2018/00928; A61B 2018/00946; A61B 2018/00958; A61B 2018/1253; A61B 2018/126; A61B 2018/1457; A61B 2018/1462; A61B 2018/1475
See application file for complete search history.

(56) References Cited

U.S. PATENT DOCUMENTS

| | | |
|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 7/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dellamagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,658,281 A | 8/1997 | Heard |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |

(56) References Cited

U.S. PATENT DOCUMENTS

| | | |
|---|---|---|
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shiley et al. |
| 9,358,065 B2 | 6/2016 | Ladtkow et al. |
| 9,439,665 B2 | 9/2016 | Marczyk et al. |
| 9,452,011 B2 | 9/2016 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0144652 A1 | 1/2003 | Baker et al. |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2010/0241119 A1 | 9/2010 | Bayat |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes |
| 2013/0066317 A1 | 3/2013 | Evans et al. |
| 2013/0079762 A1 | 3/2013 | Twomey et al. |
| 2013/0178852 A1 | 7/2013 | Allen, IV et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0276795 A1 | 9/2014 | Batchelor et al. |
| 2014/0276799 A1 | 9/2014 | Batchelor et al. |
| 2015/0119885 A1 | 4/2015 | Windgassen et al. |
| 2015/0148798 A1 | 5/2015 | Windgassen et al. |
| 2015/0320485 A1 | 11/2015 | Batchelor et al. |

FOREIGN PATENT DOCUMENTS

| | | |
|---|---|---|
| CN | 102836006 A | 12/2012 |
| EP | 0392548 A1 | 10/1994 |

(56) References Cited

FOREIGN PATENT DOCUMENTS

| | | | |
|---|---|---|---|
| EP | 1089664 | | 4/2001 |
| EP | 1530952 | | 5/2005 |
| EP | 1769765 | A1 | 4/2007 |
| EP | 1810629 | | 7/2007 |
| EP | 1977706 | | 10/2008 |
| EP | 2403422 | | 1/2012 |
| JP | H10-137259 | A | 5/1998 |
| JP | H10-504485 | A | 5/1998 |
| JP | 2000070280 | A | 3/2000 |
| JP | 2001170070 | A | 6/2001 |
| JP | 2004508875 | A | 3/2004 |
| JP | 2005144192 | A | 6/2005 |
| JP | 2005521465 | A | 7/2005 |
| JP | 2009247893 | A | 10/2009 |
| JP | 2012518490 | A | 8/2012 |
| WO | 96/005776 | A1 | 2/1996 |
| WO | 9966850 | | 12/1999 |
| WO | 02/24089 | A1 | 3/2002 |
| WO | 2006/122279 | | 11/2006 |
| WO | 2007/002545 | | 1/2007 |
| WO | 2007/093857 | | 8/2007 |
| WO | 2010/101897 | | 9/2010 |
| WO | 2012/053530 | A | 4/2012 |

OTHER PUBLICATIONS

Japanese Office Action for Application No. JP 2016-230392 dated Oct. 3, 2017.
Chinese Office Action for Application No. 201480011492.2 dated Oct. 26, 2016.
International Search Report and Written Opinion for Application No. PCT/US2014/026960 dated Jul. 21, 2014.
International Search Report and Written Opinion for Application No. PCT/US2014/027131 dated Jul. 21, 2014.
International Search Report and Written Opinion for Application No. PCT/US2014/027131 dated Jul. 30, 2014.
Potentially related U.S. Appl. No. 14/177,780, filed Feb. 11, 2014.
Potentially related U.S. Appl. No. 14/178,411, filed Feb. 12, 2014.
Potentially related U.S. Appl. No. 14/209,071, filed Mar. 13, 2014.
Potentially related U.S. Appl. No. 14/205,598, filed Mar. 12, 2014.
Potentially related U.S. Appl. No. 14/205,919, filed Mar. 12, 2014.
Potentially related to U.S. Appl. No. 14/206,010, filed Mar. 12, 2014.
Potentially related U.S. Appl. No. 14/210,741, filed Mar. 14, 2014.
Potentially related U.S. Appl. No. 14/211,042, filed Mar. 14, 2014.
Potentially related U.S. Appl. No. 14/178,569, filed Feb. 12, 2014.
Potentially related U.S. Appl. No. 14/178,577, filed Feb. 12, 2014.
315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
Potentially related U.S. Appl. No. 14/589,482, filed Jan. 5, 2015, Published as US2015/0148798.
Potentially related U.S. Appl. No. 14/589,515, filed Jan. 5, 2015, Published as US2015/0119885.
Potentially related U.S. Appl. No. 14/829,725, filed Aug. 19, 2015.
Potentially related U.S. Appl. No. 14/830,069, filed Aug. 19, 2015.
Potentially related U.S. Appl. No. 14/830,255, filed Aug. 19, 2015.

COMBINATION ELECTROSURGICAL DEVICE

FIELD

The present teachings generally relate to an electrosurgical device that can supply both monopolar power and bipolar power during a surgical procedure, and specifically to electrical forceps that can be mechanically reconfigured and/or electrically reconfigured to provide both monopolar power and bipolar power during open surgery.

BACKGROUND

Typically, electrosurgical devices have stand-alone monopolar capabilities or bipolar capabilities. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for the surgical procedure the surgeon may use either the device that supplies monopolar power to perform the procedure or switch to a device with bipolar capabilities. Both of these devices may be used to perform the procedure, however, switching between devices and/or using a device that may be better suited for a different purpose may disturb the procedure flow, cause unnecessary delays in the procedure, and in some cases result in less than optimal energy sources being used.

Generally, electrosurgical devices are connected to a generator that produces a therapy signal and provides power to the electrosurgical device so that a therapy current is produced. However, the therapy currents that may be used are limited by the generator and thus if the generator is only capable of producing a single therapy current then only one therapy current can be applied through the electrosurgical device. Additionally, a generator may be capable of producing two therapy circuits, but the electrosurgical device may only be capable of controlling and applying a single therapy current. Thus, the electrosurgical device may only apply a single therapy current. Some attempts have been made to produce a device that includes both monopolar capabilities and bipolar capabilities in a single device.

Examples of some electrosurgical instruments may be found in U.S. Pat. Nos. 6,110,171; 6,113,596; 6,190,386; 6,358,268; and 7,232,440; and U.S. Patent Application Publication Nos. 2005/0113827; 2005/0187512; 2006/0084973; and 2012/0123405 all of which are incorporated by reference herein for all purposes. It would be attractive to have an electrosurgical device that may be switched between a first electrosurgical configuration (e.g., a bipolar configuration) and a second electrosurgical configuration (e.g., a monopolar configuration) with one hand so that a user can easily perform a desired task without the need to disrupt the flow of a procedure. It would be attractive to have an electrosurgical device that may be used in open surgery as forceps and may be used for electrical cutting and/or hemostasis. What is needed is an electrosurgical device with both monopolar capabilities and bipolar capabilities where the monopolar capabilities are deactivated during use as a bipolar device and where the forceps are immobilized during use as a monopolar device. What is needed is an electrosurgical device that produces more therapy currents than a generator supplies signals (i.e., generator modes) to the electrosurgical device. What is needed is an electrosurgical device that is electrically reconfigurable so that the electrosurgical device has fewer activation buttons then signals that the generator supplies (i.e., generator modes) yet is capable of being electrically reconfigured to apply all of the signals from the generator.

SUMMARY

The present teachings meet one or more of the present needs by providing: an electrosurgical device: forceps having: a first working arm, a second working arm, wherein the electrosurgical device has a first electrosurgical configuration where the first working arm and the second working arm are in an opposed position so that the forceps deliver a first therapy current that flows between the first working arm and the second working arm; and wherein the electrosurgical device has a second electrosurgical configuration when the first working arm, the second working arm, or both are repositionable relative to each other so that the first working arm is extended with respect to the second working arm or vice versa and a second therapy current is delivered from the first working arm to a remote electrode.

Another possible embodiment of the present teachings comprises: an electrosurgical system comprising: a handpiece including: a first working arm, a second working arm, and an activation circuit having a first switch state and a second switch state, wherein a therapy current is conducted between the first working arm and the second working arm when the activation circuit is in the second switch state and the handpiece is in a first position; wherein the therapy current is conducted between the first working arm or the second working arm, and an adjacent handpiece component when the activation circuit is in the second switch state and the handpiece is in a second position; and wherein the therapy current is not conducted when the activation circuit is in the first switch state.

Yet another possible embodiment of the present teachings provides: an electrosurgical system comprising: a handpiece including: a first power connector; a second power connector; and one or more moveable members having a first position and a second position; and an activation circuit having a first switch state and a second switch state, wherein the activation circuit in the first switch state does not allow either a first electrosurgical therapy signal or a second electrosurgical therapy signal to exit the handpiece; wherein when the activation circuit is in the second state and the one or more moveable members are in the first position the activation circuit allows the first electrosurgical therapy signal to exit the handpiece so that a first therapy current extends between the first power connector and the second power connector, and wherein when the activation circuit is in the second state and the one or more moveable members are in the second position the activation circuit allows the second electrosurgical therapy signal to exit the handpiece so that a second therapy current extends between the first power connector and the second power connector The teachings herein provide an electrosurgical device that may be switched between a first electrosurgical configuration (e.g., a bipolar configuration) and a second electrosurgical configuration (e.g., monopolar configuration) with one hand so that a user can easily perform a desired task without the need to disrupt the flow of a procedure. The teachings herein provide an electrosurgical device that may be used in open surgery as forceps and may be used for electrical cutting and/or hemostasis. The teachings herein provide an electrosurgical device with both monopolar capabilities and bipolar capabilities where the monopolar capabilities are deactivated during use as a bipolar device and where the forceps are immobilized during use as a monopolar device. The teachings herein provide an electrosurgical device that produces more therapy currents than a generator supplies signals (i.e., generator modes) to the electrosurgical device. The present teachings provide an electrosurgical device that is electrically reconfigurable so that the electrosurgical device has fewer activation buttons then signals that the generator supplies (i.e., generator modes) yet is capable of being electrically reconfigured to apply all of the signals from the generator.

DETAILED DESCRIPTION

Figure 1:
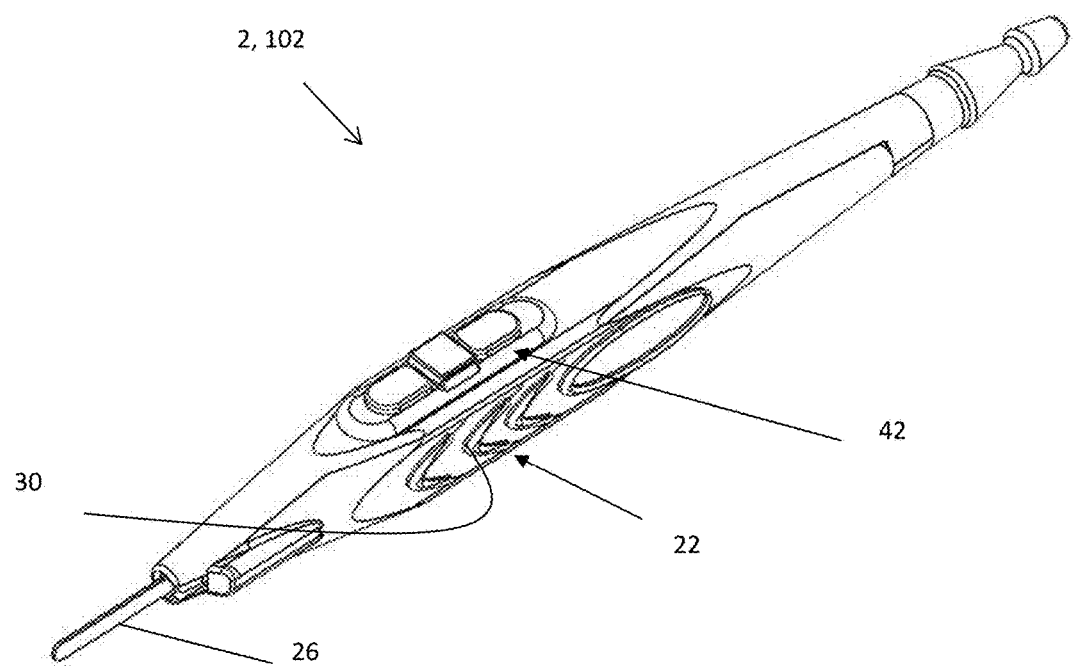
FIG. 1 illustrates an electrosurgical device in a monopolar configuration.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application No. 61/787,731, filed on Mar. 15, 2013 and 61/864,157, filed on Aug. 9, 2013 the contents of which are incorporated by reference herein in their entirety for all purposes. The present teachings relate to an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. More preferably, the electrosurgical system includes an electrosurgical device electrically connected to a generator. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both. For example, the electrosurgical device may be switched between a monopolar configuration, a bipolar configuration, or a combination of both. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate fulgurate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof. The electrosurgical device may include a handpiece and a generator. The electrosurgical device may have one or more therapy signals that extend between the handpiece and the generator.

The one or more therapy signals may be a signal, power, continuity, or a combination thereof. The one or more therapy signals may extend from the handpiece to the generator or vice versa. The one or more therapy signals may be formed by the handpiece, formed by the generator, or both. The electrosurgical therapy signals may be a therapy current. Preferably, the electrosurgical therapy signals indicate that a user has performed a step and a signal is being transmitted so that therapy current, energy, or both is generated. The electrosurgical therapy signals may provide a signal so that one or more therapy currents are produced and the therapy currents may be used for electrosurgery. The electrosurgical therapy signal may be conducted when the activation circuit is in the first switch state, the second switch state, a third switch state, the handpiece is in a first position, a second position, a third position, or a combination of switch states and handpiece positions. Preferably, a therapy signal is not generated, does not exit the handpiece, or both when the activation circuit is in the first switch state. The electrosurgical therapy signal may be a monopolar therapy signal, a bipolar therapy signal, or both. The electrosurgical therapy signal may be a monopolar generator signal, a bipolar generator signal, or both. The monopolar therapy signal may be any signal that has a voltage differential between a return port and an active port in the generator. The monopolar therapy signal may be any signal that when applied by the electrosurgical device extends: from one pole of an electrosurgical device to another pole located at a remote location, off of the electrosurgical device (e.g., from the handpiece to a location separate from the handpiece), off of the handpiece, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from a movable member to one or both working arms, or both). An electrosurgical therapy signal, when the activation circuit is in the second state, may exit the handpiece so that a therapy current extends from a moveable member, between the first working arm and the second working arm, between the moveable member and one or both of the working arms, or a combination thereof. The therapy signal may be generated and conducted from the handpiece to the generator.

The generator may function to supply: power, a therapy current, control signals, an electrosurgical therapy signal, electrically reconfigures itself in response to a signal from the user and/or mechanical reconfiguration by the user, physically reconfigures in response to adjustments by the user, or a combination thereof. The generator may function to electrically connected to a handpiece to provide and/or receive electrosurgical therapy signals, power, therapy current, or a combination thereof. The generator may be capable of producing only a single therapy current. The generator may be capable of producing two therapy currents. The generator may be capable of producing a plurality of therapy signals. The therapy currents produced by the generator may be provided by a voltage source in the generator or connected to the generator. The generator may include a voltage source, provide a voltage source, be connected to a voltage source, transmit a voltage source, or a combination thereof. The voltage source may be activated by one or more signals from the internal switches and/or CPU, the activation circuit, or both. The voltage source may provide power to the handpiece, the electrosurgical device, the working arms, the bipolar arm, the monopolar electrode, through one or more pins, or a combination thereof. The generator may include two or more power connections or three or more power connections. The power connections may be any pin in the generator so that one or more power connectors of the handpiece may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU). The CPU and the switches of the generator may perform the same function. The CPU, the switches, or both may be interchanged to power the electrosurgical device. The CPU may electrically reconfigure the electrosurgical device without the need for physical reconfiguration. The CPU may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to switch the electrosurgical device between first electrosurgical configuration, a second electrosurgical configuration, a third electrosurgical configuration, a monopolar configuration, a bipolar configuration, a non-electrosurgical configuration, or a combination thereof.

The first electrosurgical configuration, second electrosurgical configuration, and third electrosurgical configuration may be any configuration such that the electrosurgical device is mechanically reconfigured, electrically reconfigured, signally reconfigured and/or different, or a combination thereof. The first electrosurgical configuration, second electrosurgical configuration, and third electrosurgical configuration may be any of the various configurations discussed herein. The first electrosurgical configuration may provide a first therapy current.

The first therapy current may be monopolar energy and/or monopolar current. Preferably, the first therapy current is bipolar energy and/or bipolar current. Bipolar energy may be any power source that during application extends from one pole of an electrosurgical device to another pole on the electrosurgical device. Stated another way, bipolar energy is energy that extends from one component of the handpiece to another component of the handpiece. Preferably, between two physically connected components of the handpiece. For example, energy that extends between two working arms on the handpiece is bipolar energy. The first electrosurgical configuration may be deactivated by electrically disconnecting the one or more first activation buttons, deactivating the one or more first activation buttons, covering the one or more first activation buttons, electrically disconnecting all or a portion of an activation circuit, covering the one or more first activation buttons, or a combination thereof. The first electrosurgical configuration may be deactivated and a second electrosurgical configuration activated.

The second electrosurgical configuration may provide a second therapy current. The second therapy current may be bipolar energy (e.g., bipolar current or bipolar power).

Preferably, the second therapy current may be monopolar energy (e.g., monopolar current or monopolar power). Monopolar energy may be any power source that during application extends from one pole of an electrosurgical device to another pole located at a remote location, off of the electrosurgical device, off the handpiece, or a combination thereof. Stated another way, monopolar energy is energy that extends from one component of the handpiece to a component that is not physically part of the handpiece. For example, energy that extends from one or both working arms to a remote electrode (e.g., ground pad), which may be directly and/or indirectly electrically connected, is monopolar energy. The second electrosurgical configuration may be deactivated by electrically disconnecting the one or more second activation buttons, electrically disconnecting all or a portion of an activation circuit, covering the one or more second activation buttons, electrically disconnecting one or both working arms, shorting the first working arm with the second working arm, or a combination thereof. Deactivating the second electrosurgical configuration may only deactivate the second electrosurgical configuration, disconnect the second electrical configuration, deactivate both the first electrosurgical configuration and the second electrosurgical configuration, may deactivate so that a third electrosurgical configuration may be used, covering the second activation button and/or the third activation button, or a combination thereof.

The third electrosurgical configuration may be any electrosurgical configuration, a non-electrosurgical configuration, or both so that the electrosurgical device may be used to perform a procedure. Preferably, the third electrosurgical configuration is a non-electrosurgical configuration. The non-electrosurgical configuration may be any configuration where power is not supplied to the handpiece, the two or more working arms, or a combination thereof. The non-electrosurgical configuration may be used when the electrosurgical device is being used as forceps, tweezers, a clamp, Kelley hemostat forceps, scalpel, or a combination thereof. In the non-electrosurgical configuration the working arms may be mobile. In the non-electrosurgical configuration the working arms may be immobilized. In the non-electrosurgical configuration the therapy current may not pass through the handpiece, the working arms, the electrosurgical device, or a combination thereof.

The therapy current that extends through the handpiece may be effected by a signal and or current from the generator; a switch state of the activation circuit (e.g. first switch state, second switch state, third switch state, etc. . . . ); a hand piece position (e.g., first position, second position, third position, etc. . . . ); or a combination thereof. For example, the therapy current may be monopolar energy when the handpiece is in the second position and the activation circuit is in the second switch state. However, the therapy current may be bipolar energy when the handpiece is in the second position. In another example, the therapy current may be a bipolar energy when the handpiece is in the first position and the activation circuit is in the first switch state. The first switch state may be an open switch, an open circuit, or both. The second switch state may be a closed circuit, may power the activation circuit, may transmit a signal, or a combination thereof. The first electrosurgical configuration, second electrosurgical configuration, and third electrosurgical configuration may be any configuration that may perform one or more of the functions as discussed herein for the monopolar configuration, bipolar configuration, and non-electrosurgical configuration and each of those functions is incorporated herein. Preferably, as discussed herein the first electrosurgical configuration is a bipolar configuration, the second electrosurgical configuration is a monopolar configuration, and the third electrosurgical configuration is a non-electrosurgical configuration.

The device when in a monopolar configuration may supply power through a handpiece component (e.g., a working arm and/or a monopolar electrode) and a return electrode (e.g., a ground pad) that may be located at another location outside of the hand held portion of the electrosurgical device, through a handpiece component and an adjacent handpiece component, or both. The monopolar configuration may be any configuration where the electrosurgical device may be used to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. A monopolar configuration may be used so that power during use extends from one or more working arms or one or more remote electrodes (e.g., ground pads) so that the one or more extended working arms may be used for delicate electrosurgery, localized electrosurgery, coagulation, cutting, or a combination thereof. The monopolar electrosurgery may be used for less delicate procedures, less localized electrosurgery, or both when compared to bipolar electrosurgery. The monopolar electrosurgery therapy current may extend a greater distance when compared to bipolar electrosurgery. The monopolar therapy current may extend from a monopolar electrode to a ground pad.

The ground pad may function to complete a circuit, act as a second pole of a device, be located at a distal location and receive power from the monopolar electrode and/or a working arm, or a combination thereof. The ground pad may be located a distance from the handpiece so that power flows from the monopolar electrode to the ground pad. The ground pad may be on when the electrosurgical system is in a monopolar configuration, a bipolar configuration, or both. Preferably, the ground pad is only powered when the electrosurgical system is in the monopolar configuration. More preferably, the ground pad may be turned off in a bipolar configuration.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The device when in the bipolar configuration may supply power between two localized handpiece components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The forceps may function to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps include at least two working arms.

The working arms may be any part of the electrosurgical device that may be used to grip, hold, squeeze, or a combination thereof an object when the object is between the two or more opposing working arms. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position one or both of the working arms are immobilized so that the working arms cannot be used a forceps. The working arms may be longitudinally static and moveable relative to each other. Preferably, at least one of the working arms is both longitudinally movable (e.g., movable along the length of the handpiece) and laterally movable (e.g., movable towards and away from an opposing working arm). More preferably, one working arm is longitudinally movable (e.g., retractable) and one working arm is longitudinally static. The longitudinally static working arm may be a monopolar electrode. The monopolar electrode may apply a monopolar therapy current. The monopolar electrode may remain extended in the monopolar configuration. Power may be applied between the monopolar electrode and the ground pad. The monopolar electrode may apply power to the ground pad when the bipolar arm is retracted. The bipolar arm may be a working arm that is movable between a retracted position and an extended position. Power may be applied between the bipolar arm and the monopolar electrode. The bipolar arm may be movable between a bipolar position (e.g., extended) and a monopolar position (e.g., retracted). The working arms may be longitudinally moveable and may be moveable relative to each other so that a gripping force may be created. The working arms may be retractable and/or extendable individually, simultaneously, or both. The working arms may be selectively retractable and/or extendable so that one or more tip regions are exposed.

The working arms may include a tip region. The tip region may include a portion that is configured to assist in facilitating gripping, holding, squeezing, or a combination thereof tissue, an organ, skin, a vein, a feature of interest, or a combination thereof. The tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The working arms may include an active portion and an inactive portion (i.e., an insulated portion).

The active portion may be any portion of the device that may be used to apply power. The active portion may be the same portion as the contact regions, the tip region, or both of the forceps. Thus, for example, when tissue is grasped between the contact portions of the forceps, power may be supplied to the tissue through this contact portion. The active portion of the working arms preferably is between the two opposing working arms, the active portion during a monopolar configuration is part of a single working arm, or both. The active portions may be substantially surrounded by inactive portions or portions that are insulated. The inactive portion may be any portion that does not supply power, that is insulated, or both. The inactive portion may prevent stray current from passing from the handpiece, one or both working arms, the monopolar electrode, the bipolar arm, or a combination thereof. The inactive portion may be any portion that may prevent a transfer power through incidental contact and thus are insulated so that an incidental transfer of power does not occur. For example, an outside of the working arms may be coated with an insulating material so that if the working arms accidentally contact tissue proximate to the tissue of interest the proximate tissue is not subjected to a transfer of power. The inactive portion and the active portion may be made of different materials, coated with different materials, or both.

The working arms may be made of any material that may be used to grip, hold, squeeze, or a combination thereof and provide monopolar power, bipolar power, a therapy current, a gripping force, or a combination thereof to a desired location. The working arms may be made of one material and the tip region of each working arm may include, be coated with, or both one or more materials that may be insulating, a higher thermal conductivity than the base material, a lower thermal conductivity than the base material, or a combination thereof. Each of the working arms include a material with a thermal conductivity and the thermal conductivity of the working arms may be the same, one working arm may be higher than the other working arm. The one or more working arms may include one or more materials along the length of the working arm. For example, the working arms may be entirely made of stainless steel. Preferably, each working arm includes two or more materials. For example, the working arms may have a base material of stainless steel and the working arms may be coated with an insulating material such as silicone or polytetrafluoroethylene (PTFE). The working arms may include any material that is safe for use in a surgical procedure, and preferably and electrosurgical procedure. The working arms may include metals, plastics, a polymer, an elastomer, gold, silver, copper, titanium, aluminum, iron based metals, stainless steel, silicone, polytetrafluoroethylene (PTFE), insulating polymers, rubber, or a combination thereof. Preferably, each working arm is substantially coated with an insulating material except for a contact region between the two working arms where the working arms contact each other. The working arms may be coated in regions where the user contacts the working arms. The working arms may have an active portion and a passive portion, an inactive portion, or both. For example, the active portion may be the metal that extends through the working arms and is used to provide monopolar energy, bipolar energy, gripping capabilities, holding capabilities, squeezing capabilities, or a combination thereof. The passive portion may be a portion that houses the active portion. The passive portion may be a housing.

The working arms may be located within a housing. The working arms may be moved into and out of the housing so that in some positions the housing insulates the working arms. The housing may be any part of the device that may include one or more working arms and be gripped by a user during use. The housing may electrically connect, mechanically connect, or both the two working arms. The housing may be a pivot point so that the two working arms may be moved when the housing is compressed. The housing may substantially surround the working arms so that only the tip regions extending out of the housing and are exposed. The housing may surround an outer side of the working arms and an inner side of the working arms may be exposed. The housing may be electrically connected to a power source and provide power to each of the working arms. The housing may be electrically insulating. The housing may include one or more activation buttons, one or more activation circuits, one or more printed circuit boards and associated controls, one or more shuttles, one or more wires, one or more conductors, or a combination thereof.

The two or more working arms may be immobilized by an immobilization feature. The immoblization feature may be any feature that immobilizes one or both of the working arms so that the forceps are disabled in the monopolar configuration (e.g., the working arms are prevented from laterally moving). The immobilization features may be part of the arms, part of the housing, all or a part of the shuttle, or a combination thereof. The immobilization features may be a track that extends along all or a portion of each arm and as the shuttle is moved forward or backward to the monopolar configuration, each track may extend into communication with the shuttle so that each of the working arms are moved into contact with each other and vice versa from the bipolar configuration. The immobilization feature may be a lock, a fastener, a piece that houses all or a portion of the working arms, or a combination thereof that locks the two working arms together, locks one or both working arms in a retracted position, prevents both working arms from being simultaneously retracted, or a combination thereof. The immobilization feature may be a piece that slides and compresses the working arms, a piece that twists and radially compresses the working arms, or a combination of both. The immobilization feature may be connected to, include, be separate from, or a combination thereof a bias device.

The bias device may function to retract and/or advance one or more components of the electrosurgical device. The bias device may function to separate the working arms of the electrosurgical device when in the bipolar configuration. The bias device may push the shuttle forward into a bipolar configuration, pull one or both of the working arms back to form a monopolar configuration, or a combination thereof. The bias device may ensure that the shuttle, working arms, a movable member, or a combination thereof are in a fully extended and/or fully retracted state. For example, if a user moves a shuttle towards a forward position and stops short, the bias device may complete the movement to a final position. The bias device may assist in moving any of the devices and/or features discussed herein so that the devices and/or features are bi-stable. For example, the bias device may ensure that the working arms are always either fully extended or fully retracted and not located therebetween. The bias device may be a spring, a piece of rubber, an elastomeric piece, a bend in metal that forms a bias surface, or a combination thereof. If the bias device is bent metal the metal may curve so that the bias device extends in more than one plane. For example, the bias device may be bent so that the bias device is substantially "J" shaped and the tip of the "J" may be bent towards the body of the "J" so that a spring force is created. The first plane may contact a first surface and the second arm may contact a second surface so that two opposing electrosurgical components are moved. The bias device may be ramped so that a working arm, a moveable member, or both may be extended away from the handpiece, may be moved into a second plane, biased, or a combination thereof. The bias device may be connected to a shuttle, between the working arms, on an end of one or both working arms, or a combination thereof.

The shuttle may be any device that covers one or more activation buttons, moves one or both working arms, immobilizes and/or electrically disconnects one or more features of the electrosurgical device and/or activation circuit, immobilizes one or more activation buttons, impedes movement and/or depression of one or more activation buttons, or a combination thereof. The shuttle may be a shield that covers the activation buttons that are not in use so that one or more of the activation buttons are protected from contact. For example, when the electrosurgical device is configured for bipolar use, the shuttle may cover the monopolar activation buttons and expose the bipolar activation buttons or vice versa. The shuttle may include a device that extends under, around, though, or a combination thereof one or more activation buttons so that movement of the one or more activation buttons is impeded, prevented, or both. For example, when the shuttle is moved a portion of the shuttle may extend under one or more of the one or more activation buttons so that a user is unable to depress the button to provide power, electricity, a therapy current, or a combination thereof. The shuttle may include one or more positions. Preferably, the shuttle includes at least a first position and a second position (i.e., a first electrosurgical configuration and a second electrosurgical configuration). The shuttle in the first position, the second position, or both may perform any of the functions discussed herein for the shuttle. The shuttle may be connected to one or more other devices that may be retracted. For example, the shuttle may be connected to one working arm and the shuttle may be used to move the working arm into and/or between a monopolar configuration and a bipolar configuration. The shuttle may be integrally connected to one or both working arms. The shuttle may lock a device in a position, immobilize one or more working arms, or both. The shuttle may lock by a detent, a projection that locks in a corresponding recess, a mechanical interlock, a friction fit, a mechanical lock, or a combination thereof. The shuttle may be connected to one or both working arms of the electrosurgical device. The shuttle may be connected to the housing and slide on a track so that when the shuttle is extended towards a monopolar position all or a portion of each working arm is contacted by the shuttle so that the arms are moved, immobilized, or both. The shuttle in a first position may activate a portion of an activation circuit and disable a portion of an activation circuit and when moved into a second position may switch so that a different portion of the activation circuit is activated and a different portion is deactivated.

The activation circuit may be any part of the electrical surgical system, handpiece, or both that may be activated so that one or more therapy currents are generated, applied, supplied, prevented from being supplied, or a combination thereof. The activation circuit may electrically connect two or more components, electrically activate two or more components, provide a user interface, may electrically connect one or more components with a generator, or a combination thereof. The activation circuit may be connected to the generator by one or more ports. Preferably, the activation circuit and generator are connected by a plurality of ports. The activation circuit may be connected to the generator by two or more ports or three or more ports. The ports may be an upper port, a middle port, a lower port, a first port, a second port, or a combination thereof. The activation circuit may include one or more switches and preferably a plurality of switches. Each of the switches may have one or more switch states. Preferably, each switch includes at least a first switch state and a second switch state. Each switch may include a neutral position (e.g., a third switch state). The activation circuit may have two or more switch states or three or more switch states. The activation circuit may have a first switch state and a second switch state. Preferably, the activation circuit has two switch states (e.g., on or off). The activation circuit may have three switch states (e.g., off, high, or low). The first switch state may be off, not provide a therapy signal, not provide a first therapy signal, not provide a second therapy signal, not provide a third therapy signal, or a combination thereof. The first switch state may prevent a therapy signal from being produced, prevent a therapy signal (e.g., a first therapy signal, a second therapy signal, etc. . . . ) from exiting a handpiece, prevent communication between the handpiece and the generator, or a combination thereof. The second switch state may be on, provide a therapy signal, provide a first therapy signal, provide a second therapy signal, provide a third therapy signal, or a combination thereof. The second switch state may provide a therapy current between the first working arm, the second working arm, the remote electrode (e.g., ground pad), a moveable member, or a combination thereof; produce a therapy signal; allow a therapy signal to exit the handpiece; allow communication between the handpiece and a generator; or a combination thereof. For example, when the ground pad is electrically disconnected and the activation circuit is in the second switch state, a therapy current may be conducted between both working arms. The activation circuit may include one or switches that each include the switch states discussed herein. Preferably, the activation circuit includes one or more activation buttons and/or is one or more activation buttons that may be moved and/or activated into the one or more switch states discussed herein. The activation circuit and/or electrosurgical device may include one or more switches, one or more selectors, or both.

The selector may function to select between one or more modes and/or one or more functions. Preferably, the selector allows a user to select between a plurality of different modes and/or functions. The selector may change voltage, current, power, duty cycle, frequency or a combination thereof sent from the voltage source to the electrosurgical device, the working arms, the handpiece, the ground pad, or a combination thereof. The selector may change modes and/or functions by changing voltage, current, duty cycle, frequency, or a combination thereof. The selector may switch between one or more ports in the activation circuit and the one or more ports may communicate to a CPU the desired electrosurgical function to perform. The selector may be automatically moved when the blade electrode is extended and retracted. Preferably, the user may set the selector to a desired mode and/or function. The selector may power one or more functions and/or modes simultaneously. The selector may adjust the ports of the generator connected to the activation circuit. The selector may select between different ports of the generator so that modes and/or functions of the generator may be changed. The electrosurgical device may include a button that locks the configuration of the blade electrode, allows the blade electrode to rotate, or both.

The one or more buttons (e.g., one or more activation buttons) may be any button that controls one or more functions of the electrosurgical device. The one or more buttons may control the bipolar power (i.e., a bipolar activation button), the monopolar power (i.e., a monopolar activation button), a bipolar cut setting, bipolar coagulation setting, a therapy current, rotation of one or both working arms, extension and/or retraction of one or both working arms, or a combination thereof. Preferably, a first button having a first color and/or configuration may be for applying a first therapy current and a second button having a second color and/or configuration may be for applying a second therapy current. The one or more buttons may be exposed and/or unlocked by the shuttle as the shuttle moves, one or both of the working arms move, or both to and/or from a monopolar configuration to a bipolar configuration or vice versa. For example, the monopolar activation button may only be exposed when the shuttle, one or both working arms, or both are in the monopolar configuration. The monopolar activation button, the bipolar activation button, or both may turn on power to the respective electrode so that power is supplied to the area of interest. One or both working arms when extended may activate a circuit, a switch, or both.

The circuit may have a switch that switches between the monopolar configuration, the bipolar configuration, or both. The switch may activate one or more of the bipolar electrodes and deactivate the remote electrode (e.g., ground pad or return pad) or vice versa; activate one or more bipolar electrodes (e.g., a single extended working arm) and deactivate one or more monopolar electrodes (e.g., a single retracted working arm) or vice versa; deactivate one bipolar electrode and leave the bipolar electrode open (i.e., not powered); deactivate the ground pad; deactivate all of the bipolar electrodes; or a combination thereof. The monopolar electrode, one or more of the bipolar electrodes, or both may be connected to an alternating current power source, a direct current power source, or both. Preferably, the monopolar electrodes, the bipolar electrodes, or both are connected to an alternating current power source. The monopolar electrodes, the bipolar electrodes, or both may be indirectly connected to a power source through a handpiece.

The handpiece may be any part of the device that the user grips, that houses one or more of the control buttons, one or more switches, one or more electrical connectors, one or more diodes, one or more capacitors, or a combination thereof. The handpiece may house all or a portion of the control circuitry, a central processing unit, or both. The handpiece may electrically connect the electrosurgical device, the electrical system, or both to the generator. The handpiece may both physically connect the functional elements of the electrosurgical device and electrically connect the elements of the electrosurgical device. The handpiece may include a housing and/or be covered by a housing. The handpiece may be a body portion of the electrosurgical device, a portion between the two or more working arms, a connector between the two or more working arms, a part that houses all or a portion of the circuitry, a part that includes an activation circuit, a part that includes one or more control buttons, or a combination thereof. Preferably, the handpiece is the portion that a surgeon grips and presses one or more buttons to apply power to a desired location. More preferably, the handpiece is a central portion that includes both buttons and one or more electrical connectors for supplying power to the electrosurgical device, one or both of the working arms, a return electrode, or a combination thereof. The handpiece may include one or more movable members, one or more handpiece components, or both that move along and/or within one or more tracks of the handpiece.

The one or more tracks may be any device that longitudinally extends along the handpiece so that one or more movable members, one or more working arms, or both may be movable along the handpiece. The one or more tracks may be an integral part of the handpiece, a discrete piece that is added to the handpiece, or both. The one or more tracks may form a tongue and groove configuration with a movable member, one or more working arms, or both so that the moveable member, the one or more working arms, or both are only longitudinally movable and not laterally moveable. The one or more tracks may extend substantially the entire length of the handpiece, a portion of the length of the handpiece, or both. Preferably, the tracks are long enough so that a moveable member, a working arm, or both may be longitudinally movable between an extended position and a retracted position. The tracks may be long enough so that one of the working arms may be retracted so that a tip of the working arm in the retracted position does not extend beyond the working arm. Preferably, the tracks are two generally parallel edges that extend along a longitudinal axis and include a gap between the edges so that a guide lock extends between the edges. The tracks may extend along the length of the handpiece in a way so that the moveable member, one or both working arms, or both extend and retract in a straight line. Preferably, the tracks extend at an angle so that the moveable member, one or both working arms, or both are moved towards the handpiece during retraction (e.g., into a position so that they are protected by the handpiece) and away from the handpiece during extension. The one or more tracks may curve at a termination point so that the moveable member, one or both working arms, or both extend away from the handpiece, the guide locks exit the tracks, or both in an extended position. For example, the guide lock may exit the tracks when the guide lock reaches the termination point so that a working arm extends away from the handpiece and may be used as forceps. The one or more bias devices may work in conjunction with the tracks and the termination point. For example, the bias device may be "J" shaped and be located between two tracks and the guide lock may be maintained within the tracks until the guide lock reaches a termination point of the tracks where the tracks curve up and the bias device moves into a second plane so that the bias device moves the guide lock away from the handpiece and out of the tracks. The guide lock may further fit on a second plane of the bias device so that the guide lock is biased by the bias device and may be used as forceps. The tracks may be located on a side, an edge, or both so that the one or more working arms, one or more movable members, or both may be moved along the handpiece. One or more of the one or more tracks may include one or more guide locks.

The one or more guide locks may function to lock a moveable member, one or both working arms, or both along a length of the track and/or create a friction force on a moveable member, one or both working arms, or both so that free movement is prevented. The one or more guide locks may function to prevent movement of one or more working arms, one or more moveable members, or both in a first electrosurgical position, a second electrosurgical position, or a position therebetween. The one or more guide locks may be a piece that extends into the handpiece and forms a connection with the track, extends into the track so that a connection is formed, slides along the track, maintains the moveable member, one or both working arms, or both within the tracks. Preferably, the one or more guide locks may laterally extend from one of the one or more working arms, the moveable members, or both and assist in maintaining the one or more working arms, the moveable members, or both longitudinally along the handpiece. The one or more guide locks may form any shape so that the guide locks maintain a connection with the tracks, slide along the tracks, or both. The one or more guide locks may be "T" shaped, "1" shaped, "J" shaped, may include one or more barbs that extend from one or more sides of the guide lock, one or more projections that extend from one or more sides of the guide lock, or a combination thereof so that the one or more guide locks form a connection with the tracks, contact the tracks, or both. The one or more guide locks may maintain the moveable member, one or both working arms, or both in a retracted position (e.g., a first electrosurgical configuration), an extended position (e.g., a second electrosurgical configuration), or both. The retracted position may be any position where the moveably member, the one or both working arms, or both are moved into contact with the handpiece, are located a distance from the handpiece, or both. Preferably, in the retracted position the moveable member, one or both working arms, or both are moved substantially into contact with the handpiece so that the moveable member, one or both working arms, or both are protected from damage. In the extended position the moveable member, one or both working arms, or both may be extended away from the handpiece. Preferably, when the guide lock is on a working arm, the working arm is extended away from the handpiece in the extended position so that the working arm may be used as at least one portion of forceps. The guide lock may assist a working arm in extending towards an opposing working arm so that the working arms may be used as forceps. The guide lock when on a moveable member may assist in longitudinally moving the moveable member in a desired direction (e.g., a straight line or an arcuate movement). The one or more guide locks may be used in conjunction with one or more track detents.

The one or more track detents may function to lock and/or produce a friction force on a moveable member, one or both working arms, or both along the length of the handpiece. The one or more guide locks may contact one or more track detents so that the track detents and guide locks may prevent incidental movement of the moveable member, one or both working arms, or both. The one or more track detents may be any device that forms a complementary connection with the guide locks, with a barb on the guide lock, a projection on the guide lock, or a combination thereof. The one or more track detents may function to form a catch point and prevents movement of the moveable member, one or both working arms, or both along a longitudinal axis of the handpiece. The one or more track detents may be a series of peaks and troughs and all or a portion of the guide lock may become embedded within the trough so that movement of the guide lock is prevented, inhibited, or both. A plurality of peaks and troughs may be located along a length of the one or more track detents so that the position of the moveable member, one or both working arms, or both may be selected by a user. For example, one track detent may be located at an extension end of the handpiece when the moveable member, one or both working arms, or both is in an extension position and one track detect may be located at a retraction end of the handpiece when a moveable member, one or both working arms, or both are in a retraction position.

The one or more movable members may be any part of the handpiece that may be moved between two or more positions. The one or more movable members may be moved between a first position and a second position. The one or more movable members may be moved between a second electrosurgical configuration (e.g., a monopolar configuration) and a first electrosurgical configuration (e.g., a bipolar configuration) or vice versa. The one or more movable members may be any part of the electrosurgical device and/or electrosurgical system that may be electrically reconfigured, mechanically reconfigured, or both. The one or more movable members may be a monopolar electrode, a first working arm, a second working arm, a ground pad, or a combination thereof. The one or more movable members may be electrically connected to a first power connector, a second power connector, or both. The moveable member may be moved between one or more of the positions discussed herein for the monopolar electrode, the bipolar electrode, or both and the activation circuit between one or more switch states as discussed herein so that the moveable member is electrically configured, mechanically configured, or both in the same configuration as those respective components. The one or more movable members may be a handpiece component.

The one or more handpiece components may be any device that is directly electrically connected to the handpiece. For example, a handpiece component is electrically connected to the handpiece directly as opposed to indirectly through the generator. The one or more handpiece components may be any component that may mechanically reconfigure the handpiece, be mechanically reconfigured by the handpiece, moved along the handpiece, apply a therapy current from the handpiece, or a combination thereof. The one or more handpiece components may be electrically connected to the handpiece so that power, signals, therapy currents, or a combination thereof flow directly to and/or from the handpiece, from the handpiece component without travelling through an intervening device. Preferably, the handpiece component may be physically located separate from the handpiece but electrically connected directly to the handpiece. The one or more handpiece components and handpiece may be electrically reconfigurable so that the handpiece and the handpiece component are electrically connected in some configurations and electrically disconnected in some configurations. The one or more handpiece components may be a first working arm, a second working arm, a ground pad, a movable member, or both. Preferably, in one configuration the ground pad is placed discretely from the handpiece but the ground pad is directly electrically connected to the handpiece such that when the handpiece is in a monopolar configuration the ground pad is electrically activated. For example, the ground pad may be directly connected to a the handpiece via a bypass in the shuttle as opposed to being directly connected to a pin in the generator so that the ground pad has no direct connection to the handpiece. The handpiece may provide power to the one or more handpiece components so that the handpiece components are not electrically connected directly to a power supply, a therapy current, a generator, or a combination thereof.

The power connectors may be any device that supplies power, a therapy current, or both from a power source to the electrosurgical system, the electrosurgical device, or both so that the electrosurgical system, electrosurgical device, or both may be used for electrosurgery. The electrosurgical system, electrosurgical device, the handpiece, or a combination thereof may include one or more, preferably two or more, or most preferably two power connectors supplying power to the electrosurgical system, electrosurgical device, the handpiece, or a combination thereof. The therapy current may be any current that is applied by the electrosurgical device and performs a predetermined function. The therapy current may be monopolar power, bipolar power, coagulation, cutting, hemostasis, or a combination thereof. The therapy current may be any application of power that is produced by the electrosurgical device. The therapy current may be any application of power that extends into and through the electrosurgical device from one or more power connectors. Each of the power connectors may be directly connected to a power source, a generator, or both. For example, if the electrosurgical device has three power connectors and the generator has three power connections (e.g., pins) each power connector may be plugged separately into its own power connection. The generator may include four power connectors (e.g., four pins). The pins may be a bipolar positive pin, a bipolar negative pin, a monopolar active pin, a monopolar return pin, or a combination thereof. The pins may be connected and disconnected to each of the electrosurgical device components via a CPU or switches as is discussed herein. Each power connector may be electrically connected to a single component of the electrosurgical device. Preferably, there are two power connectors supplying power to the electrosurgical device and the electrosurgical device is electrically reconfigured between a first position and a second position, a first switch state and a second switch state, or a combination of both so that a therapy current and/or power from one of the power connectors may be supplied to two or more components of the electrosurgical device. For example, when the handpiece is in the first position, power from the first power connector may be supplied to the first working arm and power from the second power connector may be supplied to the second working arm, and when the handpiece is moved into the second position, the first power connector may be electrically connected to the monopolar electrode (e.g., a fixed working arm) and the second power connector may be electrically connected to the ground pad. One or more of the power connectors may be indirectly connected to the power source. For example, if the generator includes two power connections and the electrosurgical device includes three power connectors, two of the power connectors may be electrically connected together and plugged into a power connector. Two or more power connectors may be electrically connected by a jumper.

The jumper may be any device that may electrically connect two or more power connectors so that the power connectors can be electrically connected, signally connected, or both to the generator. The jumper may be any device that connects two electrical connectors outside of the generator so that the two or more electrical connectors may be connected to the generator. The jumper may be any device that assists in connecting two or more electrical connectors to a power source a generator or both. Two or more of the power connectors may be electrically connected inside of the handpiece, the generator, or both by one or more connectors.

The one or more connectors may be any device that internally connects two power connectors together. The one or more connectors may electrically connect the two or more working arms during use so that power may be applied through both working arms, so that a complete circuit is formed, or both. The one or more connectors may electrically connect both of the working arms together so that one electrical connector may be used to electrically connect both working arms and one electrical connector may extend to another component such as the ground pad, a moveable member, or both. The one or more connectors may be electrical wiring with the electrosurgical device. The electrical wiring may be mechanically reconfigured by movement of one or more components of the electrosurgical device. For example, the termination points of the electrical wiring may be reconfigured when one or both of the working arms are moved between a monopolar configuration and a bipolar configuration. The electrical wiring may be reconfigured when a shuttle of the electrosurgical device (e.g., handpiece) is moved between a first position and a second position. The electrical wiring may be configured so that as one or more of the working arms, the shuttle, or both are moved the electrical wiring within the working arms, the shuttle, or both are moved into contact with different power connector and/or different electrical wiring within the working arms, the shuttle, or both are moved into contact with the power connectors so that the parts of the electrosurgical device are changed. For example, when the shuttle is in a first position both working arms may be directly connected and in a second position one working arm may be powered and one ground pad may be connected by the electrical wiring extending through the second working arm. The electrical wiring may include one or more bypasses.

The one or more bypasses may function to extend a power connector through a working arm, a shuttle, or both. The one or more bypasses may extend power through a shuttle so that the working arm, the shuttle, or both are not powered and the power extends to and powers a different handpiece component. Preferably, the bypass extends through a handpiece, a working arm, a shuttle, or a combination thereof so that power bypasses the handpiece, the working arm, the shuttle, or a combination thereof. The bypass may bypass a retracted working arm, connect a ground pad, or both. The bypass may connect an activation button to a ground pad so that the ground pad completes a circuit when power is applied to the electrosurgical device.

The electrosurgical device, the activation buttons, the handpiece, activation circuit, or a combination thereof may include one or more diodes. The diodes may be in any configuration so that upon pressing of an activation button, movement of a switch, or both the generator, the electrosurgical device, or both measures a frequency, a change in frequency, or both so that the generator may determine the activation mode that is being powered. The one or more diodes may adjust a steady state AC signal from the buttons, the activation circuit, or both so that the generator supplies the selected therapy current. Preferably, the one or more diodes may be different so that the two or more different frequencies, shifts in frequency, signals, or a combination thereof are created so that a generator may determine which switches in the handpiece, the electrosurgical device, the activation buttons, or a combination thereof are open, closed, or both.

The electrosurgical device, generator, handpiece, or a combination thereof may include one or more transformers. The one or more transformers may be of any size and shape so that depending on the current path through the one or more transformers, around the one or more transformers, or both the voltage supplied through to the handpiece, the electrodes, the working arms, or a combination thereof may be varied. For example, when in a monopolar configuration the voltage may be directly delivered to the electrode and when in a bipolar configuration the transformer may step down the voltage delivered to the working arms. Conversely, the transformer may be used to increase voltage delivered to one or more electrodes.

As discussed herein various circuits may be created by electrically reconfiguring one or more components of the electrosurgical device, physically configuring one or more components of the electrosurgical device, or both. During use one or more switches may be opened and/or closed so that one or more open circuits, one or more closed circuits, or both may be formed. For example, a shuttle electrode (e.g., working arm) may be extended forward so that a connection is formed between the electrode and a power source and the ground pad and a power source so that a circuit is completed and an open circuit may be created between the power source and the working arms so that the working arms are not powered. The circuits may be configured so that a circuit is created between two or more components and the electrosurgical device may be used for a desired type of electrosurgery. The electrosurgical instrument may be configured so that power flows from one or more working arms to another working arm, the ground pad, or a combination of both. The electrosurgical device may be configured with one or more power connectors, preferably two or more power connectors, and more preferably three or more power connectors. Each of the power connectors may be connected to one or more components, two or more components, or even three or more components. Each power connector may be switched between one or more components, two or more components, or even three or more components. The method may include a step of immobilizing one or more bipolar electrodes, one or more working arms, or both simultaneously.

A method of switching the electrosurgical device between a bipolar configuration, a monopolar configuration, a non-electrosurgical configuration, or a combination thereof. The method may include one or more of the steps discussed herein in virtually any order. The method may include a step of advancing a shuttle, retracting a shuttle, applying a ground pad, removing a ground pad, reconfiguring a circuit, moving a movable member, or a combination thereof. The method may include a step of applying monopolar power and then immediately subsequently applying bipolar power or vice versa. The method may include a step of cutting in a non-electrosurgical configuration and then applying either monopolar power or bipolar power to coagulate, cauterize, or both without a step of changing instruments. The method may include a step of cutting in a monopolar configuration and then coagulating, cauterizing, or both using bipolar energy without a step of changing instruments.

FIG. 1 illustrates the electrosurgical device 2 in a monopolar configuration 102. The electrosurgical device 2 is changed into a monopolar configuration 102 when the bipolar arm 30 is moved backwards into a monopolar position 22 and only the monopolar electrode 26 remains extended forward. When the monopolar activation button 42 is pressed power travels from the monopolar electrode 26 to a return electrode (not shown).

Figure 2:
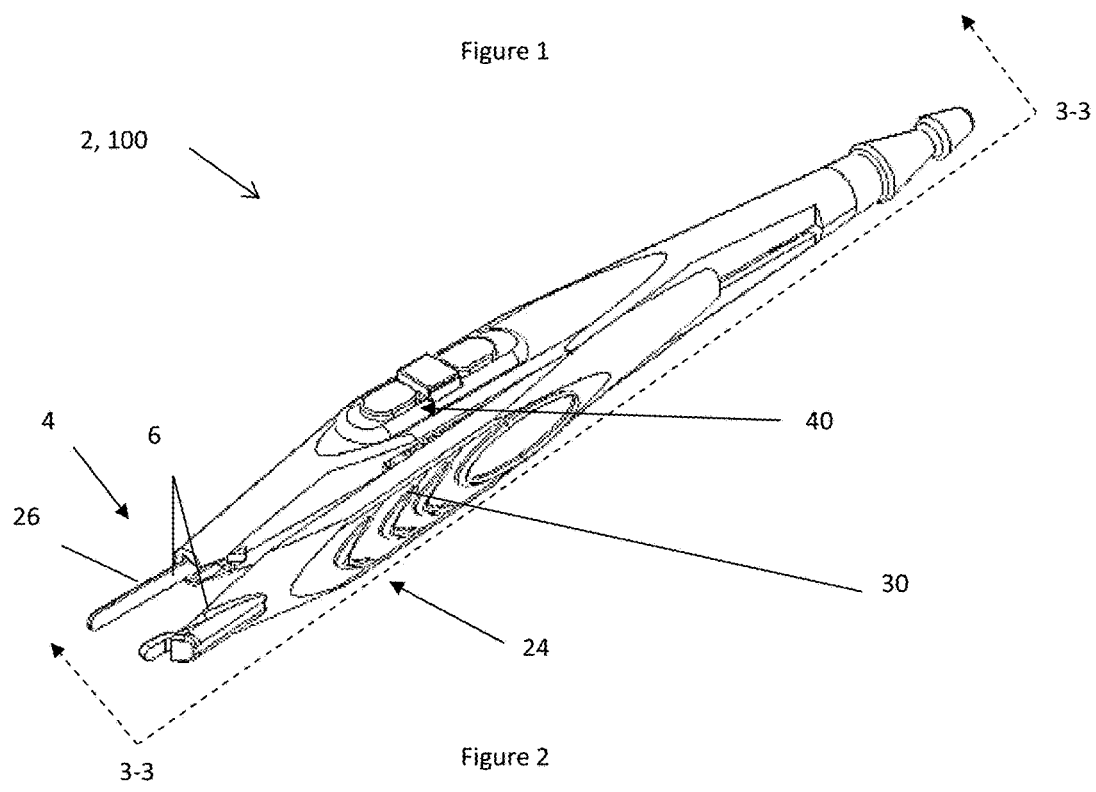
FIG. 2 illustrates the electrosurgical device of FIG. 1 in a bipolar configuration.

FIG. 2 illustrates an electrosurgical device 2. The electrosurgical device 2 includes a bipolar configuration 100 where the electrosurgical device 2 is configured as forceps 4. The forceps 4 include a pair of working arms 6 that transfer power therebetween when the bipolar activation button 40 is pressed. The bipolar arm 30 is moved into a bipolar position 24 so that the bipolar arm 30 and the monopolar electrode 26 are located proximate to each other.

Figure 3:
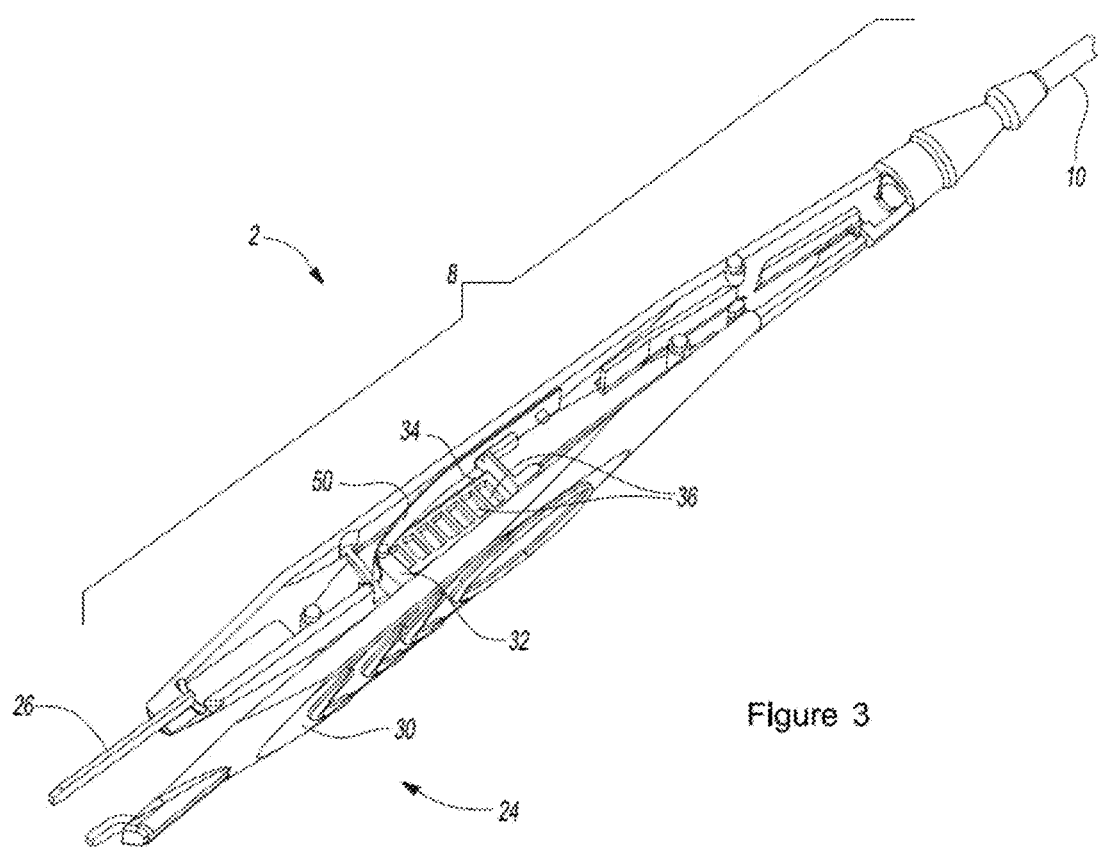
FIG. 3 illustrates a cross-sectional view of FIG. 3 along lines 3-3.

FIG. 3 illustrates a cross-section of the electrosurgical device 2 along lines 3-3. The electrosurgical device 2 includes a handpiece 8 that power connectors 10 run through to provide power to the monopolar electrode 26 and the bipolar arm 30 so that monopolar power and/or bipolar power can be used. The bipolar arm 30 includes a guide lock 32 that extends between the bipolar arm 30 and the handpiece 8. The guide lock 32 locks the bipolar arm 30 in the bipolar position 24 as shown when the bipolar arm 30 is fully extended. The guide lock 32 extends into a track 34 that assists in positioning the bipolar arm 30 as the bipolar arm 30 is moved from the bipolar position 24 to the monopolar position 22 as is illustrated in FIG. 1. The handpiece 8 includes a plurality of track detents 36 that extend along the length of the handpiece 8 so that as the guide lock 32 is moved between a monopolar position 22 (as is illustrated in FIG. 1) and a bipolar position 24 (as is illustrated in FIG. 2) or vice versa resistance is applied to the guide lock 32 to provide control and a smooth movement to the user. A bias device 50 is located within the handpiece 8 and extends between the handpiece 8 and the bipolar arm 30 so that when the bipolar arm 30 is moved forward into the bipolar position 24 the bias device 50 assists in extending the bipolar arm 30 away from the monopolar electrode 22. When in the bipolar position 24 the bias device 50 provides resistance to the bipolar arm 30 so that the bipolar arm 30 is not inadvertently retracted during use. As illustrated, the bias device 50 is a piece of spring steel that extends from a back side of the handpiece 8 to a front side of the handpiece 8 so that as the bipolar arm 30 approaches the bipolar position 24 the bias device 50 curves and produces a force on the guide lock 32 moving the bipolar arm away from the handpiece 8. The bias device 50 further acts to move the bipolar arm 30 away from the monopolar electrode 26 so that the working arms can be used as forceps.

Figure 4:
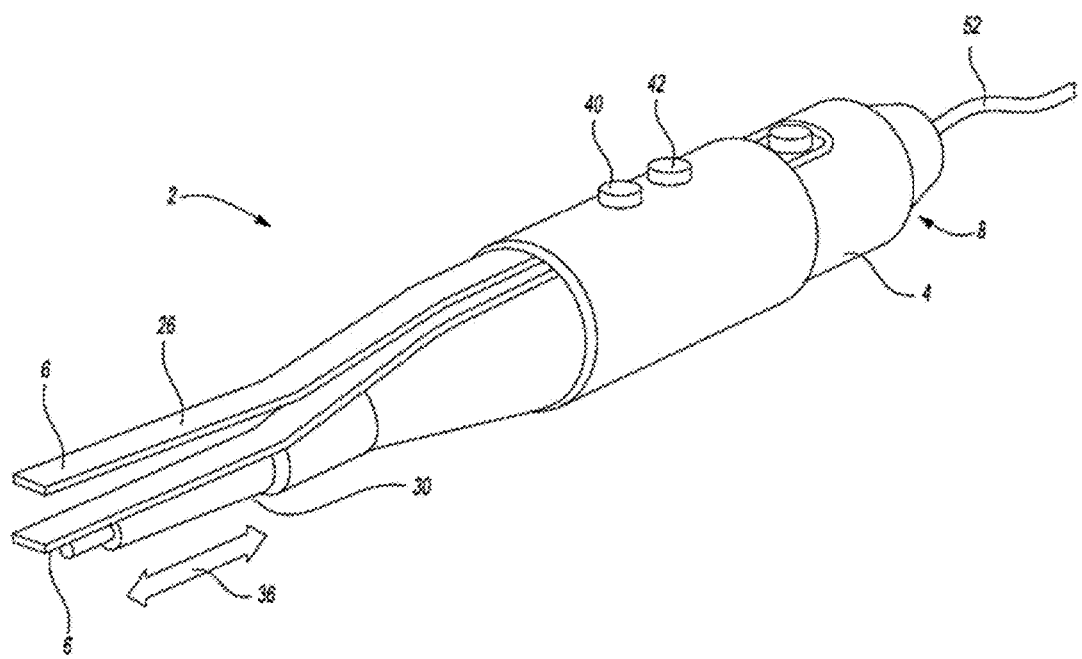
FIG. 4 illustrates a view of another example of an electrosurgical device being switched between a monopolar configuration and a bipolar configuration.

FIG. 4 illustrates another configuration of the electrosurgical device 2 configured as forceps 4. The electrosurgical device 2 includes a handpiece 8 with a pair of working arms 6 extending therefrom. One of the working arms 6 is a static monopolar electrode 26 that is used for supplying both monopolar power and bipolar power. The other working arm 6 is a bipolar arm 30 that is movable in the direction 36 between a bipolar position and a monopolar position. The handpiece 8 includes a bipolar activation button 40 and a monopolar activation button 42, and a power connection 52 for providing power to the electrosurgical device 2.

Figure 5:
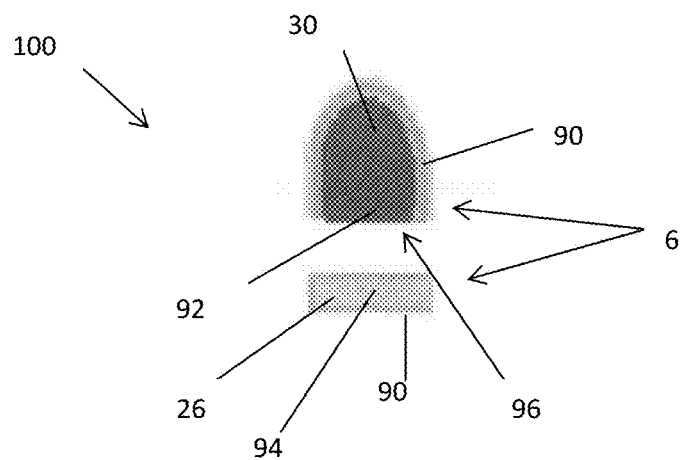
FIG. 5 illustrates an example of one configuration of the tips of an electrosurgical device in a bipolar configuration.

FIG. 5 illustrates an end view of one possible bipolar configuration 100. As illustrated, each of the working arms 6 are made of two materials. The outer portion of both of the working arms 6 is made of a material with insulating thermal conductivity 90. The monopolar electrode 26 includes a material with low thermal conductivity 94 located within the material with insulating thermal conductivity 90. The bipolar arm 30 includes a material with insulating thermal conductivity 90 around the outside, but is free of the material with insulating thermal conductivity 90 in a contact region 96 so that the material with high thermal conductivity 92 is exposed.

Figure 6:
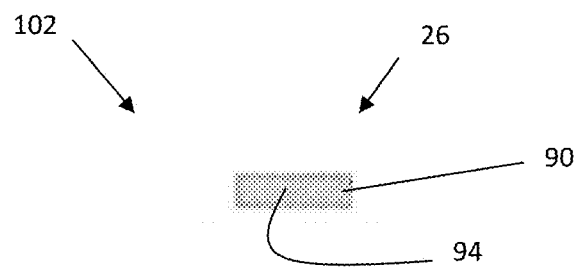
FIG. 6 illustrates an example of one configuration of a tip of an electrosurgical device in a monopolar configuration.

FIG. 6 illustrated the monopolar configuration 102. As illustrated the monopolar electrode 26 includes a material with insulating thermal conductivity 90 around an outside of the monopolar electrode 28 with a material with low thermal conductivity 94 extending beyond the material with the insulating conductivity 90 so that monopolar power can be supplied.

Figure 7A:
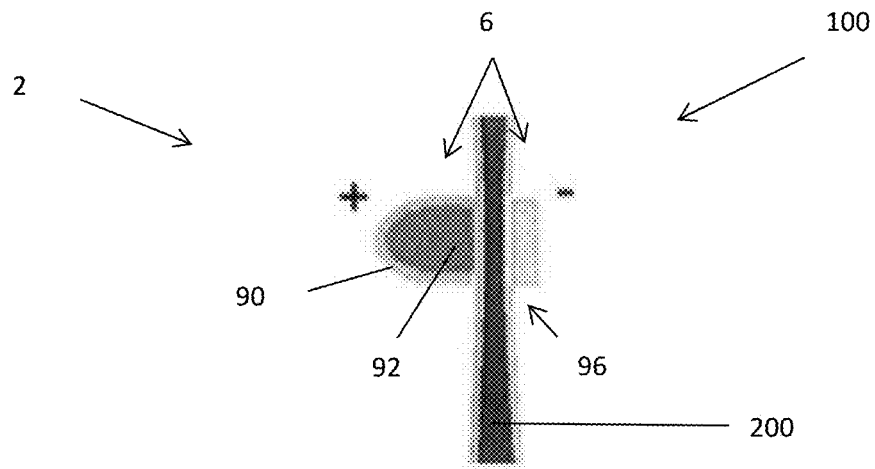
FIG. 7A illustrates an example of a bipolar configuration during use.
Figure 7B:
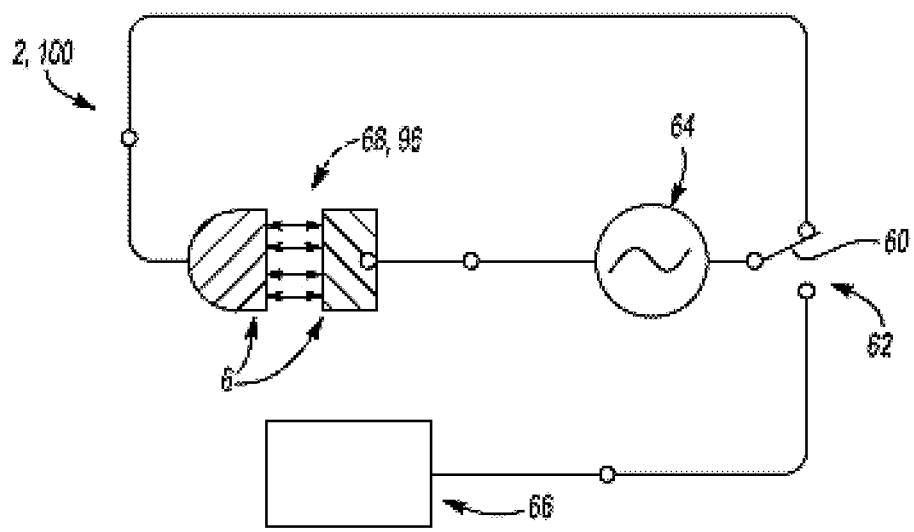
FIG. 7B illustrates a circuit diagram of the electrosurgical device in a bipolar configuration.

FIGS. 7A and 7B illustrate the electrosurgical device 2 during use in the bipolar configuration 100. FIG. 7A illustrates the pair of working arms 6 having a material with insulating thermal conductivity 90 and a material with high thermal conductivity 92. The working arms 6 are shown gripping tissue 200 in the contact region 96 so that power flows from one working arm 6 through the tissue 200 to the other working arm 6.

FIG. 7B is a circuit diagram illustrating one possible bipolar circuit configuration 100 of the electrosurgical device 2. The electrosurgical device 2 is connected to a voltage source 64, and power flows through a switch 60 through the working arms 6 so that a completed circuit is formed. When the switch 60 is moved so that a circuit is formed between the two working arms 6 an open circuit 62 is formed between the circuit and the ground pad 66 so that the ground pad 66 is electrically disconnected. As illustrated, the power flows 68 from one working arm 6 thorough tissue 200 (not shown) located in the contact region 96 to the other working arm 6.

Figure 8A:
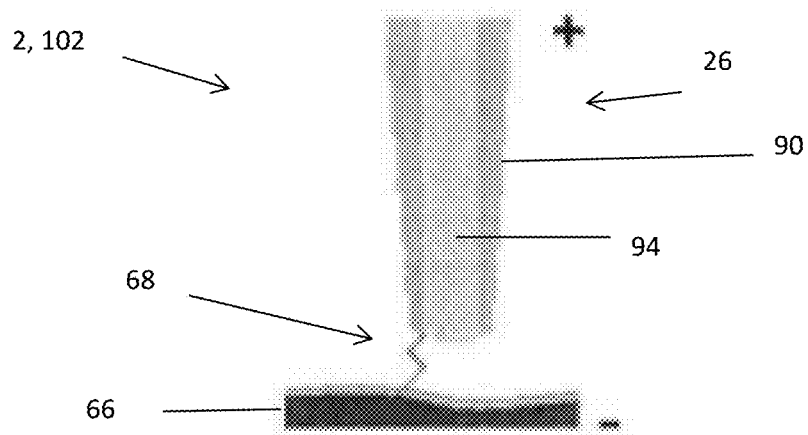
FIG. 8A illustrates another possible configuration of an electrosurgical device in a monopolar configuration.
Figure 8B:
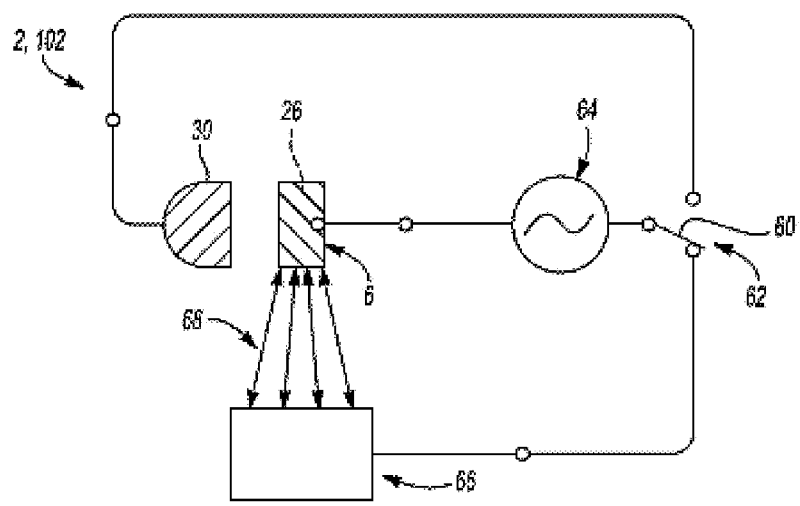
FIG. 8B illustrates a circuit diagram of the electrosurgical device in a bipolar configuration.

FIGS. 8A and 8B illustrate the electrosurgical device 2 in a monopolar configuration 102. FIG. 8A illustrates the monopolar electrode 26 having power flow 68 to a ground pad 66, at a distal location, through tissue 200 (not shown). As illustrated, the monopolar electrode 26 includes an outer material having insulating thermal conductivity 90 and an inner material having low thermal conductivity 94 and the power flows from the inner material having low thermal conductivity 94 that is exposed at an end of the monopolar electrode 26.

FIG. 8B illustrates a circuit diagram showing one possible monopolar circuit configuration 102 of the electrosurgical device 2. The electrosurgical device 2 is connected to a voltage source 64, and power flows 68 through a switch 60 from the voltage source 64 to the ground pad 66. When the switch 60 is moved into the monopolar configuration 102 an open circuit 62 is formed between the voltage source 64 and a bipolar arm 30 so that the bipolar portion of the circuit and associated working arm 6 is disconnected and is free of power. When power is applied to the monopolar electrode 26 power flows 68 from the monopolar electrode 26 through tissue 200 (not shown) to the ground pad 66. The bipolar arm 30 and the monopolar electrode 26 as illustrated are made of different materials; however, they may be made of the same material. The bipolar arm 30 and the monopolar electrode 26 as illustrated have cross-sections with a different shape; however, the cross-sections may have the same shape (see e.g., FIGS. 2-4 and 9-13).

Figure 9A:
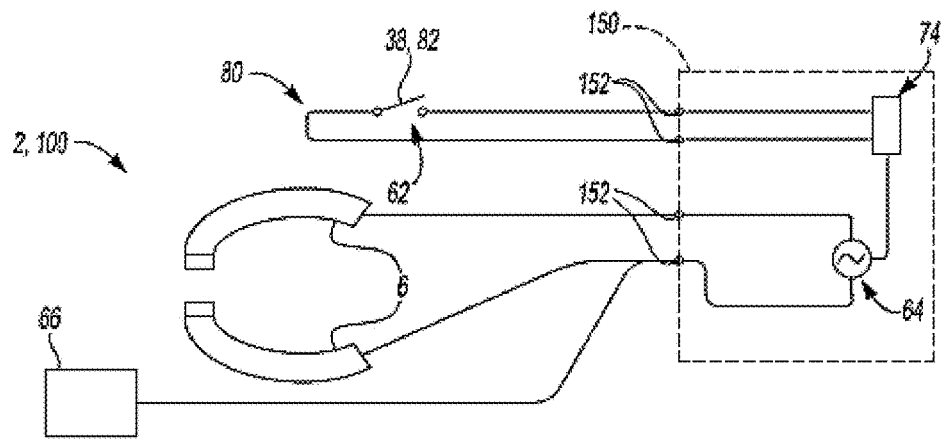
FIG. 9A illustrates an example a circuit diagram with an electrosurgical device in an off position.
Figure 9B:
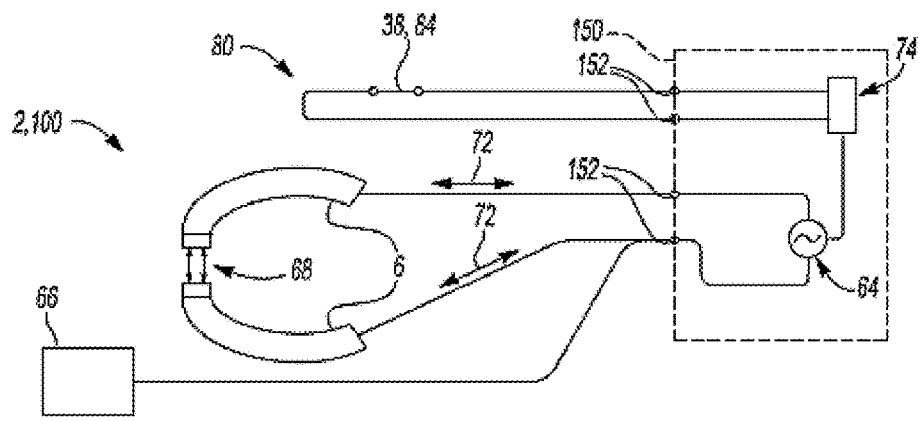
FIG. 9B illustrates an example a circuit diagram with an electrosurgical device in a bipolar configuration.
Figure 9C:
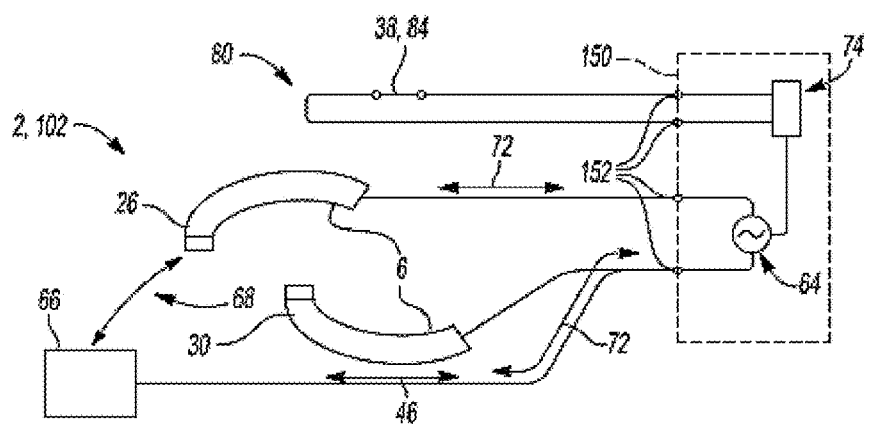
FIG. 9C illustrates an example a circuit diagram with an electrosurgical device in a monopolar configuration.

FIGS. 9A-9C illustrates mechanical reconfiguration of the electrosurgical device between a bipolar configuration 100 and a monopolar configuration 102. FIG. 9A illustrates the electrosurgical device 2 in the bipolar configuration 100 with the working arms 6 both extended. The electrosurgical device 2 includes an activation circuit 80 that has an activation button 38 in a first switch state 82 forming an open circuit 62 so that the electrosurgical device 2 is off. The activation circuit 80 is connected to the generator 150 via a pair of pins 152 that connect to an internal switch and/or central processing unit (CPU) 74. The internal switch and/or CPU 74 is connected to a voltage source 64 that supplies power to the electrosurgical device through a pair of pins 152 that connect the electrosurgical device 2 to the generator 150. The pair of working arms 6 are in the bipolar configuration 100 and a ground pad 66 is located adjacent to the working arms 6.

FIG. 9B illustrates the electrosurgical device 2 in a bipolar configuration 100 with the working arms 6 both extended. The electrosurgical device 2 includes an activation circuit 80 that has the activation button 38 in the second switch state 84 forming a closed circuit so that power 68 flows between the working arms 6. The activation button 38 when moved to the second switch state 84 supplies a signal to the generator 150 though the pins 152 so that internal switch and/or CPU 74 provides a signal and power is supplied from the power source 62 though both pins 152 to both working arms 6. Power 72 flows from the generator to each of the working arms 6 and power 68 flows between each of the working arms 6, however, as illustrated power 68 does not flow to the adjacent ground pad 66.

FIG. 9C illustrates the electrosurgical device 2 in the monopolar configuration 102 with one working arm 6 (a monopolar electrode 26) that is extended and one working arm 6 (a bipolar arm 30) that retracted in the direction 46. The activation circuit 80 includes an activation button 38 that is in the second switch state 84 forming a closed circuit and sending a signal to an internal switch and/or CPU 74 so that power 68 flows between the extended working arm 6 (monopolar electrode 26) and the ground pad 66. The activation button 38 when moved to the second switch state 84 supplies a signal to the generator through the pins 152 so that power is supplied from the power source 62 in the direction 72 through one pin to the monopolar electrode 26 and returned from the ground pad 66 in the direction 72 through the second pin 152.

Figure 10A:
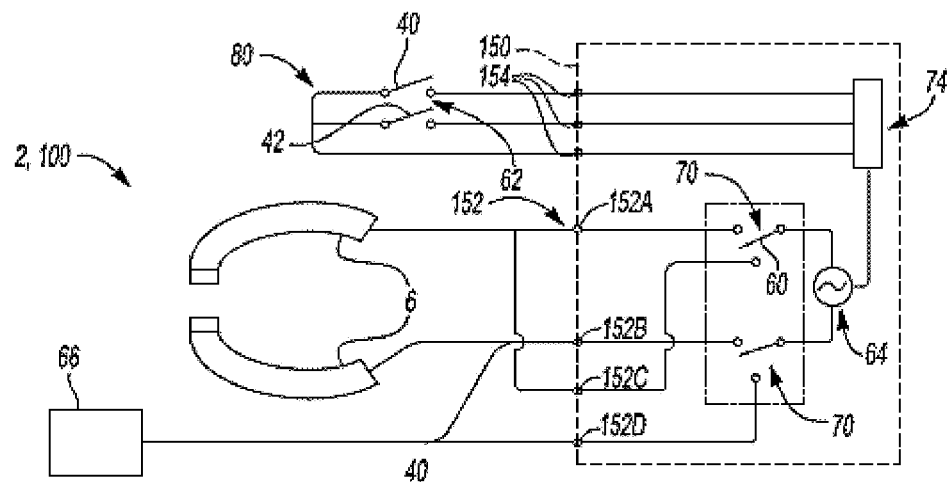
FIG. 10A illustrates an example a circuit diagram with an electrosurgical device in an off position.

FIG. 10A-10D illustrate another example of an electrosurgical device 2 changing between a bipolar configuration 100 and a monopolar configuration 102 and a cut configuration and a coagulation configuration. FIG. 10A illustrates an activation circuit 80 including a first activation button 40 and a second activation button 42. Both the first activation button 40 and the second activation button 42 are open 62 so that the electrosurgical device 2 is off. The activation circuit 80 is connected to a generator 150 by a plurality of pins 154. The plurality of pins 154 connect the activation circuit 80 to an internal switch and/or CPU 74 which when activated provides power to the electrosurgical device 2 through pins 152. As illustrated, the switches 60 are in a neutral position 70 so that power does not flow from the voltage source 64 to the electrosurgical device 2 (alternatively these switches may be open or closed and the circuit will still be off, when the activation circuit 80 has an open circuit 62). The plurality of pins 152 between the generator 150 and the electrosurgical device 2 include a bipolar positive pin 152A, a bipolar negative pin 152B, a monopolar active pin 152C, and a monopolar return pin 152D so that the working arms 6 and ground pad 66 are electrically connected to the generator 150.

Figure 10B:
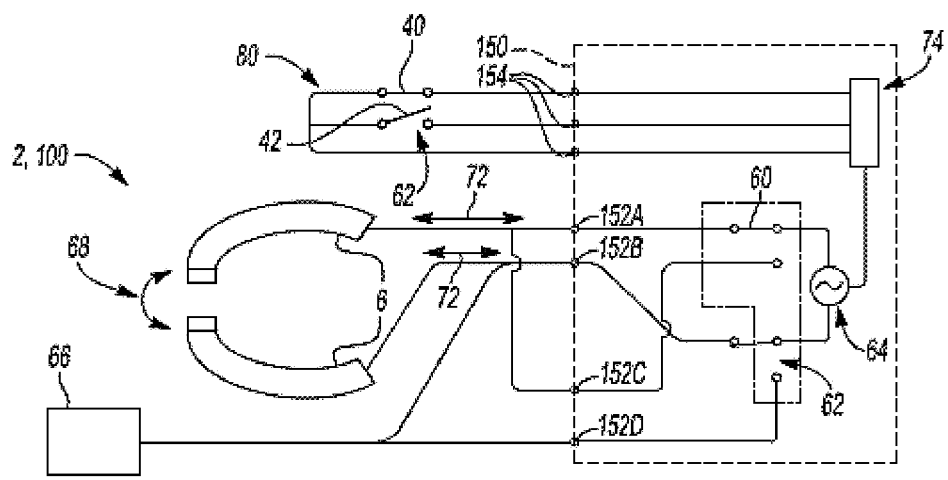
FIG. 10B illustrates an example a circuit diagram with an electrosurgical device in a bipolar configuration.

FIG. 10B illustrates the working arms 6 of the electrosurgical device 2 in a bipolar configuration 100 with power 68 extending between the working arms 6. The electrosurgical device 2 includes an activation circuit 80 with a first activation button 40 which is closed and a second activation button 42 that is open 62. Upon a signal being provided from the activation circuit 80 to the internal switch and/or CPU 74 sends signals and/or movement of the bipolar arm 30 so that the switch 60 is moved to the bipolar positive pin 152A. Similarly, the other switch 60 is moved to the bipolar negative pin 152B. The monopolar electrode 26 and bipolar arm 30 both remain extended and power 68 flows in the direction 72 from a bipolar positive pin 152A and the bipolar negative pin 152B between the working arms 6.

Figure 10C:
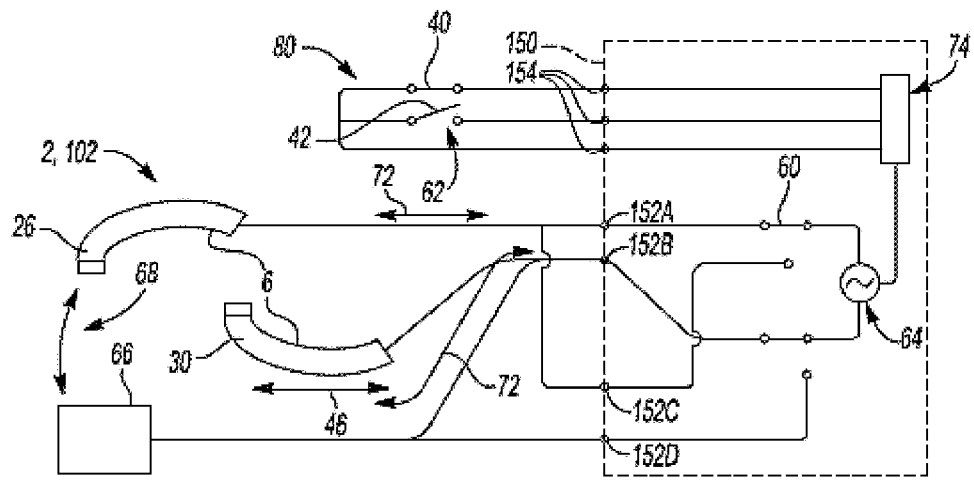
FIG. 10C illustrates an example a circuit diagram with an electrosurgical device in a monopolar coagulation configuration.

FIG. 10C illustrates a monopolar electrode 26 extended and a bipolar arm 30 retracted in the direction 46 so that power travels along the path 72 from bipolar positive pin 152A and power travels from bipolar negative pin 152B along path 72 so that a coagulation signal is generated when the first activation button of the activation circuit 80 is closed. The remaining configuration of the electrosurgical device 2 remains the same as FIG. 10B except for the bipolar arm 30 being retracted.

Figure 10D:
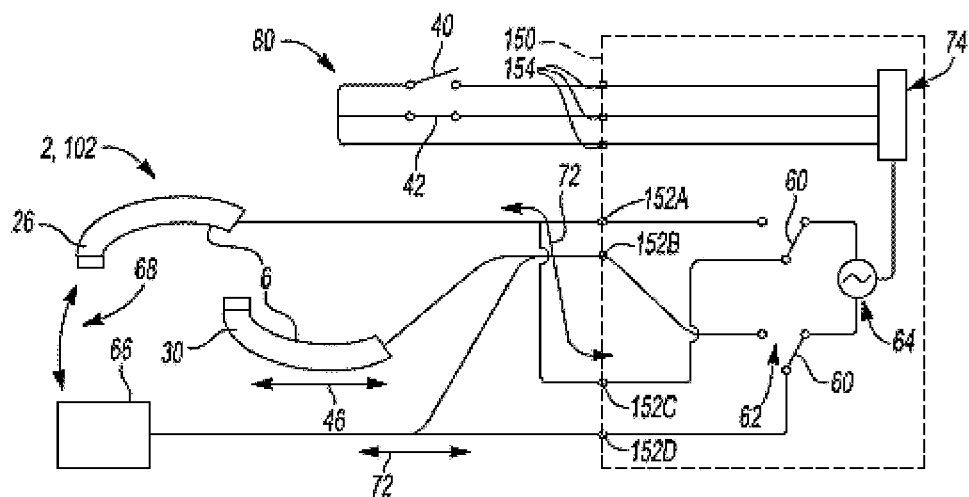
FIG. 10D illustrates an example a circuit diagram with an electrosurgical device in a monopolar cut configuration.

FIG. 10D illustrates a reconfiguration from the power 68 being a coagulation signal as is shown in FIG. 10C to a cut signal as is shown in FIG. 10D. As configured the second activation button 42 is closed and the first activation button 40 is open. When the circuit in the generator 150 is reconfigured the switch 60 that is connected to the monopolar electrode is switched from bipolar positive pin 152A to monopolar active pin 152C so that power travels in the direction 72, and the other switch 60 is switched from the bipolar negative pin 152B to the monopolar return pin 152D.

Figure 11A:
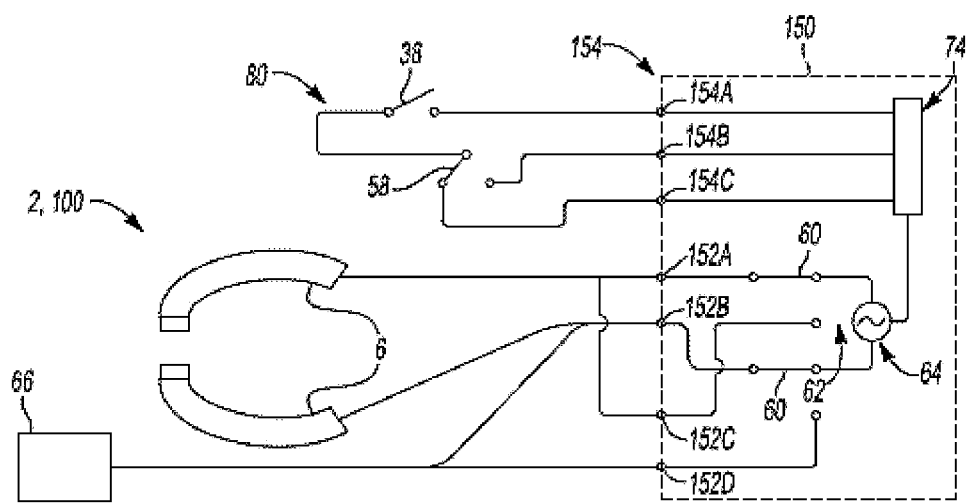
FIG. 11A illustrates an example of a circuit diagram with an electrosurgical device in device in an off position.

FIGS. 11A through 11D illustrate an example of reconfiguration from a monopolar configuration 102 to a bipolar configuration 100. FIG. 11A illustrates an electrosurgical device 2 in a bipolar configuration 100. The electrosurgical device 2 includes an activation circuit 80 that is connected to a generator via a plurality of ports 154. The activation circuit 80 includes an activation button 38 and a selector 58 and as illustrated the activation button 38 is open such that no power is supplied to the working arms. As illustrated the activation button 38 transmits a signal through upper port 154A and the selector 58 transmits a signal through the lower port 154C and the middle port 154B is not connected to any switches. The signal is transmitted through the ports 154 to the internal switch and/or CPU 74. A signal passes from the internal switch and/or CPU 74 to the voltage source 64 so that power passes from the voltage source 64 through the switches 60 and through the bipolar positive pin 152A and the bipolar negative pin 152B.

Figure 11B:
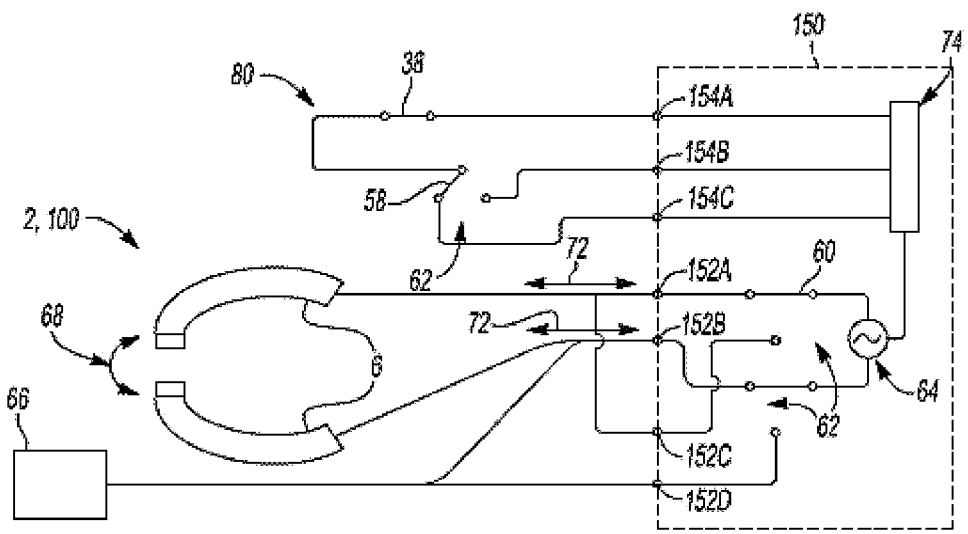
FIG. 11B illustrates an example of a circuit diagram with an electrosurgical device in device in a bipolar configuration.

FIG. 11B illustrates an activation circuit 80 with the activation button 38 being closed so that a signal passes through the upper port 154A and the selector 58, which is closed so that a signal passes through the lower port 154C to complete a circuit. The middle port 154B has an open circuit 62. The signal passes through the ports 154 to the internal switch and/or CPU 74 so that the voltage source 64 supplies power in the direction 72 to the working arms 6 via the bipolar positive pin 152A and the bipolar negative pin 152B.

Figure 11C:
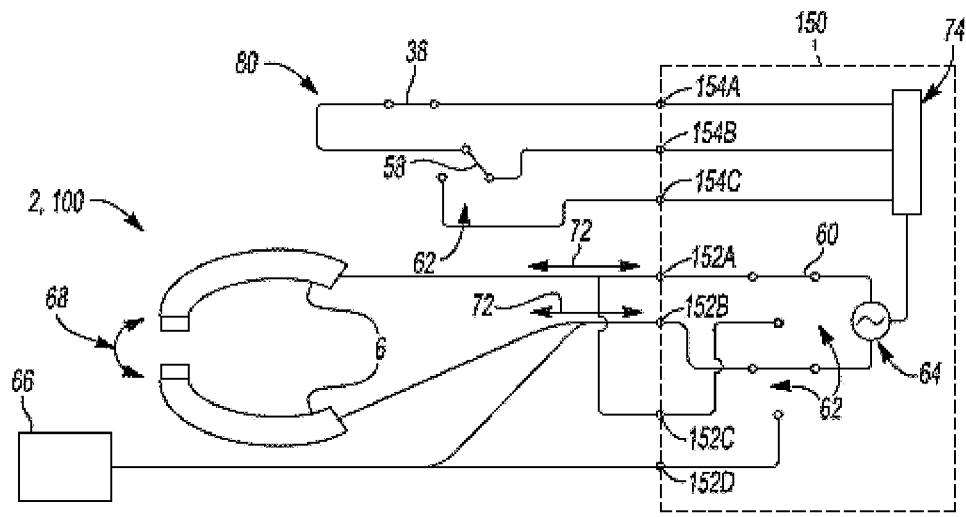
FIG. 11C illustrates an example of a circuit diagram with an electrosurgical device in device in an alternative bipolar configuration.

FIG. 11C illustrates reconfiguration from FIG. 11B where the selector 58 is moved from the lower pin 154C to the middle pin 154B so that a different voltage, current, power, duty cycle, frequency or a combination thereof are sent from the generator 150 to the electrosurgical device 2. A signal passes through the activated ports 154A and 154B of the activation circuit 80 to the internal switching and/or CPU 74. The internal switching and/or CPU 74 transmits a signal so that the voltage source 64 supplies power in the direction 72 to the working arms 6 via the bipolar positive pin 152A and the bipolar negative pin 152B. Further, the bipolar arm 30 is moved in the direction 46. The movement of the bipolar arm 30 in the direction 46 changes the position of the switches so that one switch moves from the bipolar positive pin 152A to the monopolar active pin 152C and the other switch 60 is moved from the bipolar negative pin 152B to the monopolar return pin 152C so that power 68 extends from the monopolar electrode 26 to the ground pad 66.

Figure 11D:
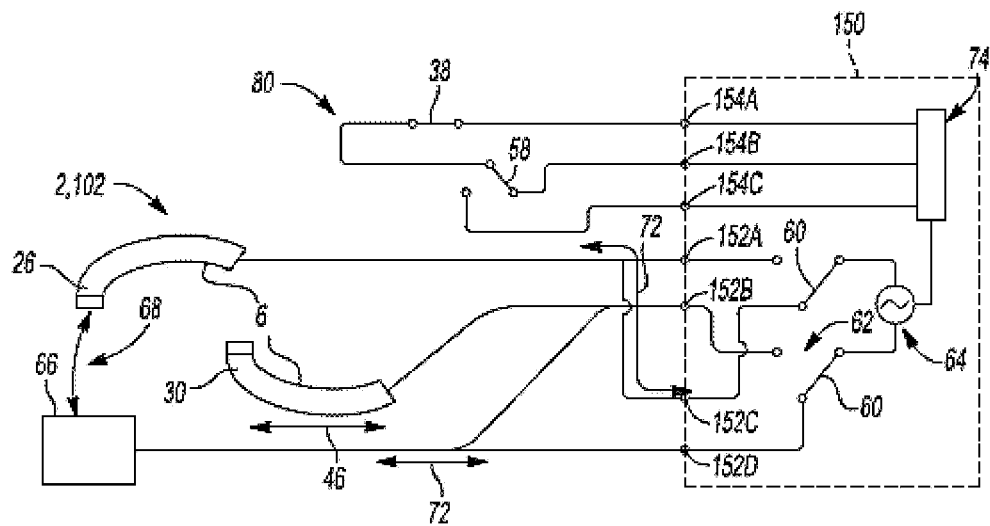
FIG. 11D illustrates an example of a circuit diagram with an electrosurgical device in a monopolar configuration.

FIG. 11D illustrates reconfiguration from FIG. 11C where the working arms 6 and electrosurgical device 2 are changed from a bipolar configuration to a monopolar configuration 102 with the monopolar electrode 26 extended and the bipolar arm 30 retracted in the direction 46. Power 68 extends from the monopolar electrode 26 to the ground pad 66. The selector 58 is moved in communication with the middle port 154B and the activation button 38 is closed so that a complete circuit is formed and a signal flows through the upper port 154A of the activation circuit 80 to the internal switch and/or CPU 74 of the generator 150. The lower port 154C is open so that the lower port 154C does not form part of the circuit. The internal switch and/or CPU 74 sends a signal so that the voltage source 64 supplies power through the switches 60 which are in communication with the monopolar active pin 152C and the monopolar return pin 152D so that power flows in the direction 72 to the ground pad 66 and the monopolar electrode 26 respectively.

Figure 12A:
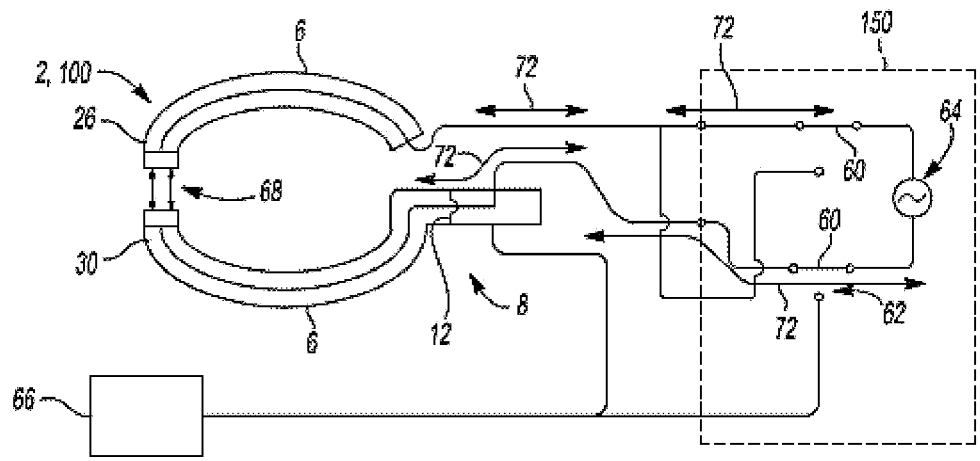
FIG. 12A illustrates an example of a circuit diagram with an electrosurgical device in a bipolar configuration.
Figure 12B:
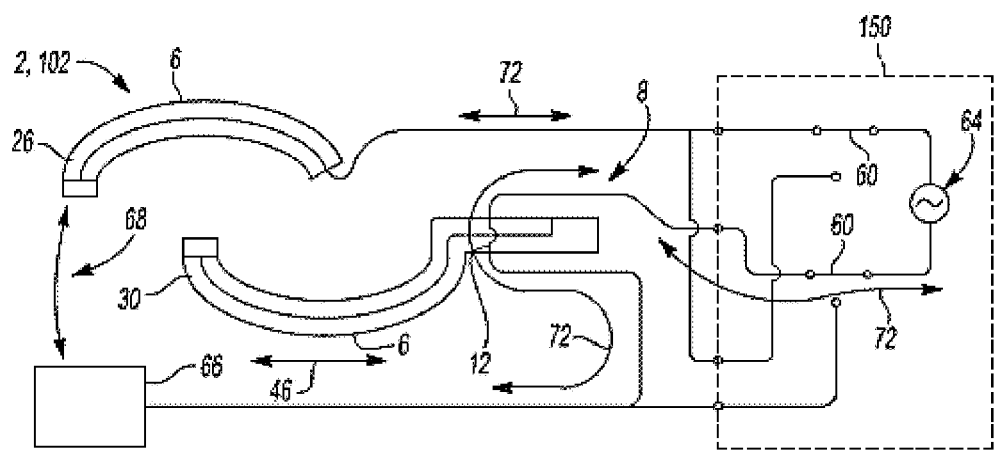
FIG. 12B illustrates an example of a circuit diagram with an electrosurgical device in a monopolar configuration.
Figure 12C:
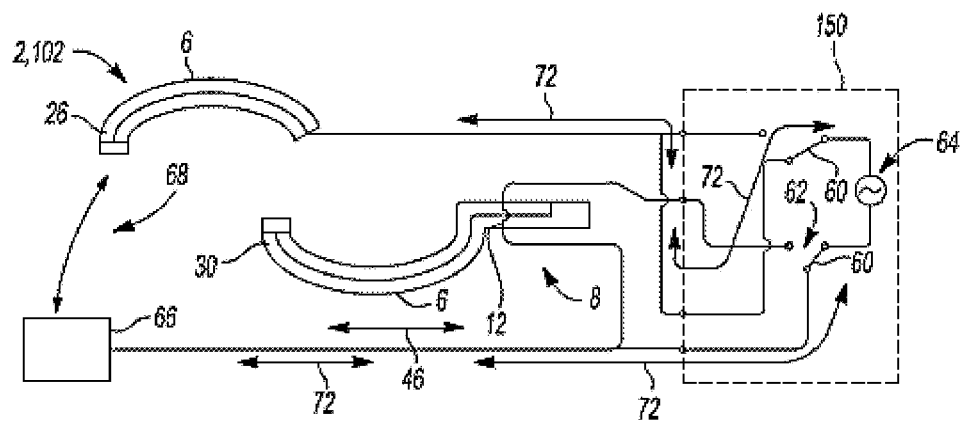
FIG. 12C illustrates an example of a circuit diagram with an electrosurgical device in an alternative monopolar configuration.

FIGS. 12A through 12C illustrate a mechanical reconfiguration of an electrosurgical device 2 from a bipolar configuration 100 to a monopolar configuration 102. The electrosurgical device 2 includes a pair of working arms 8 connected to a generator 150. FIG. 12A illustrates the monopolar electrode 26 and the bipolar arm 30 aligned so that power 68 flows between the working arms 6. The bipolar arm 30 is connected to a handpiece 8 that includes different electrical wiring such as a bypass 12. The bipolar arm 30 and handpiece 8 are connected to the generator 150 so that power flows in the direction 72 through a bipolar arm 30. The monopolar electrode 26 is connected to the generator 150 so that power flows in the direction 72 from the voltage source 64. The generator 150 includes switches 60 so that the generator is electrically reconfigured based upon the position of the switches. 60. The top switch 60 directly feeds the monopolar electrode 26 and the bottom switch directly feeds the bipolar arm 30 and the ground pad 66 has an open circuit 62 so that power is not supplied to the ground pad 66.

FIG. 12B illustrates the switches 60 in the same position as FIG. 12A and the bipolar arm 30 retracted in the direction 46 so that a bypass 12 is aligned with the flow of power 72 from the generator 150. The power extends in a serpentine pattern 72 through the bypass 12 and to the ground pad 66 so that a circuit is completed and power 68 can flow from the monopolar electrode 26 to the ground pad 66.

FIG. 12C illustrates the bipolar arm 30 retracted in the direction 46 and the switches 60 varied so that the ground pad 66 is directly connected to the voltage source 64 and power flows to the monopolar electrode 26 in the direction 72. The ground pad 66 is indirectly connected to the voltage source 64 through the bypass 12 in the handpiece 8 of monopolar electrode 26 so that power flows from the monopolar electrode 26 to the ground pad 66.

Figure 13A:
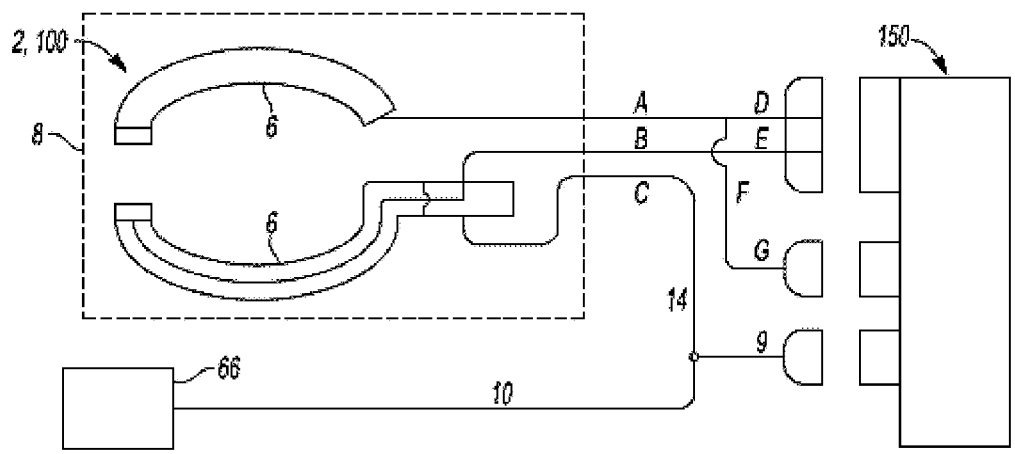
FIG. 13A illustrates an example of a circuit diagram of cables associated with the electrosurgical device.
Figure 13B:
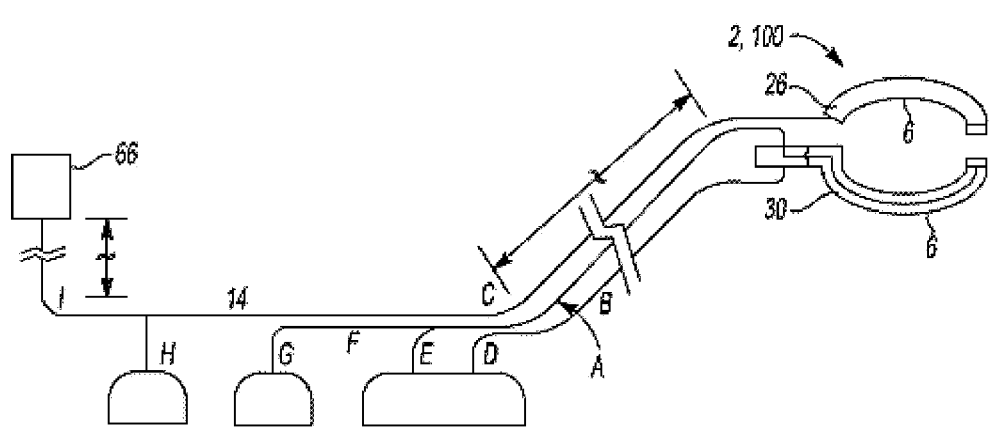
FIG. 13B illustrates another example of a circuit diagram and associated cables.

FIGS. 13A and 13B illustrates a cord management system of the electrosurgical device 2 with the electrosurgical device 2 in a bipolar configuration 100. The handpiece 8 includes a pair of working arms 6 and the working arms 6 are connected to a cable that connects the handpiece 8 to the generator 150. The cord includes lines A, B, and C. that extend from and connect to the handpiece 8. The cord splits into three prongs that connect to the generator 150. Lines A extends into the prong at point D and line B extends into the same prong at point E which is proximate to point D. Line F splits from between lines A and D and connects to a prong at point G. Line C extends from the handpiece 8 and creates a jumper 14 between the handpiece 8 and the ground pad 66 and also connects to prong H so that the ground pad 66 is connected to the generator 150.

FIG. 13B illustrates a full length of the cord of the electrosurgical device 2 of FIG. 13A. The cords are connected to the workings arms 6, which are in the bipolar configuration 100. Three cords extend from the working arms and connect to three plugs that plug into the generator (not shown). The monopolar electrode 26 is connected to a single cord that extends therefrom and includes a line C, which connects to a jumper 14 that connects line C to plug H and to the ground pad 66 at line I. The bipolar arm 30 is connected to cords A and B and cord A splits so that cord A has one line D that connects to a first plug and another line G that attaches to a second plug and lines D and G are connected by a line F. Line B is connected to the same plug as line D via line E.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrosurgical device comprising:
   forceps having:
   a first working arm,
   a second working arm,
   an immobilization feature, and
   a handpiece that a user grips during use and the handpiece includes a track that the second working arm moves along so that the second working arm is extendable and retractable;
   wherein the electrosurgical device has a first electrosurgical configuration where the first working arm and the second working arm are in an opposed position so that the forceps deliver a first therapy current that flows between the first working arm and the second working arm;

wherein the electrosurgical device has a second electrosurgical configuration when the first working arm, the second working arm, or both are repositionable relative to each other so that the first working arm is extended with respect to the second working arm or vice versa and a second therapy current is delivered from the first working arm to a remote electrode;

wherein the second working arm is immobilized in the second electrosurgical configuration by the immobilization feature so that the first working arm and the second working arm are locked together and the forceps are disabled and the second working arm is locked in a retracted position where the second working arm is moved into contact with the handpiece; and wherein the immobilization feature is a guide lock extending from the second working arm and the guide lock extends into the track so that the first working arm and the second working arm are prevented from moving relative to each other and the guide lock and the track guide the second working arm along the handpiece and assist in locking the second working arm proximate to the handpiece so that the second working arm is not damaged in the second electrosurgical configuration.

2. The electrosurgical device of claim 1, wherein the first working arm is longitudinally static and the second working arm is retractable.

3. The electrosurgical device of claim 1, wherein the handpiece includes one or more track detents along the track so that during movement of the second working arm, the guide lock forms a connection with one of the one or more track detents to temporarily maintain the second working arm along a length of the track.

4. The electrosurgical device of claim 3, wherein the one or more guide locks include one or more projections that extend from one or more sides of the guide lock and the one or more projections extend into the one or more track detents to restrict longitudinal movement of the second working arm along the first working arm.

5. The electrosurgical device of claim 1, wherein a bias device is located within the handpiece so that when the second working arm is fully extended the bias device extends a guide lock of the second working arm from the track in the handpiece.

6. The electrosurgical device of claim 5, wherein the bias device is ramped so that the bias device biases the second working arm away from the handpiece so that the forceps are formed and the first working arm and the second working arm are biased away from each other.

7. The electrosurgical device of claim 6, wherein the second working arm is electrically disabled when the second working arm is retracted.

8. The electrosurgical device of claim 1, wherein the second working arm is retractable along a longitudinal axis of the electrosurgical device.

9. The electrosurgical device of claim 1, wherein during retraction of the second working arm, the second working arm is moved towards the first working arm and then along a longitudinal axis of the electrosurgical device.

10. The electrosurgical device of claim 1, wherein the first working arm includes a first material with a first thermal conductivity and the second working arm includes a second material with a second thermal conductivity, and the first thermal conductivity is higher than the second thermal conductivity.

11. The electrosurgical device of claim 1, wherein the first working arm and the second working arm are connected together by the handpiece and the immobilization feature locks the second working arm in the second electrosurgical configuration so that the second working arm is compressed against the handpiece.

12. An electrosurgical device comprising:
forceps having:
a first working arm,
a second working arm, and
an immobilization feature;

wherein the electrosurgical device has a first electrosurgical configuration where the first working arm and the second working arm are in an opposed position so that the forceps deliver a first therapy current that flows between the first working arm and the second working arm;

wherein the electrosurgical device has a second electrosurgical configuration when the first working arm, the second working arm, or both are repositionable relative to each other so that the first working arm is extended with respect to the second working arm or vice versa and a second therapy current is delivered from the first working arm to a remote electrode; and wherein the second working arm is immobilized in the second electrosurgical configuration by the immobilization feature so that the first working arm and the second working arm are locked together and the forceps are disabled and the second working arm is locked in a retracted position where the second working arm is moved into contact with the handpiece;

wherein the immobilization feature includes one or more guide locks connected to and extending from the first working arm or the second working arm, the one or more guide locks being movable into and out of a handpiece of the forceps when the electrosurgical device is in the first electrosurgical configuration, and the one or more guide locks are located within the forceps when the electrosurgical device is in the second electrosurgical configuration so that the one or more guide locks lock the first working arm and the second working arm together and the second working arm is locked in the retracted position.

13. The electrosurgical device of claim 12, wherein the first working arm, the second working arm, or both are retractable along a longitudinal axis of the electrosurgical device.

14. The electrosurgical device of claim 3, wherein the first working arm is static and the second working arm is retractable.

15. The electrosurgical device of claim 12, wherein the forceps have a handpiece that a user grips during use and the handpiece includes a track that the second working arm moves along so that the second working arm is extendable and retractable.

16. The electrosurgical device of claim 15, the guide lock extends into the track so that the guide lock and the track guide the second working arm along the handpiece and assist in locking the second working arm proximate to the handpiece so that the second working arm is not damaged in the second electrosurgical configuration.

17. The electrosurgical device of claim 12, wherein the one or more guide locks include one or more projections that extend from one or more sides of the guide lock, include one or more barbs extending from one or more sides of the guide lock, are "T" shaped, or a combination thereof.

18. The electrosurgical device of claim 12, wherein the forceps include:
   a. a handpiece that connects the first working arm and the second working arm and
   b. a bias device is located within the handpiece; wherein the bias device is ramped so that as the second working arm moves along the handpiece, the one or more guide locks contact the bias device and biases the second working arm away from the first working arm, and the bias device provides resistance to the second working arm as the second working arm is moved towards the first working arm.

* * * * *